(12) United States Patent
Nagamine et al.

(10) Patent No.: US 9,678,423 B2
(45) Date of Patent: Jun. 13, 2017

(54) RESIST COMPOSITION, METHOD FOR FORMING RESIST PATTERN, ACID GENERATOR AND COMPOUND

(71) Applicant: TOKYO OHKA KOGYO CO., LTD., Kawasaki-shi (JP)

(72) Inventors: Takashi Nagamine, Kawasaki (JP); Hideto Nito, Kawasaki (JP); Daichi Takaki, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 15/072,004

(22) Filed: Mar. 16, 2016

(65) Prior Publication Data
US 2016/0274458 A1 Sep. 22, 2016

(30) Foreign Application Priority Data

Mar. 20, 2015 (JP) .................. 2015-058676

(51) Int. Cl.
| | |
|---|---|
| C07J 31/00 | (2006.01) |
| G03F 7/004 | (2006.01) |
| G03F 7/038 | (2006.01) |
| G03F 7/039 | (2006.01) |
| G03F 7/20 | (2006.01) |
| G03F 7/32 | (2006.01) |

(52) U.S. Cl.
CPC .......... *G03F 7/0045* (2013.01); *C07J 31/006* (2013.01); *G03F 7/038* (2013.01); *G03F 7/20* (2013.01); *G03F 7/325* (2013.01)

(58) Field of Classification Search
None
See application file for complete search history.

(56) References Cited

U.S. PATENT DOCUMENTS

| | | | | |
|---|---|---|---|---|
| 2002/0042018 A1* | 4/2002 | Maeda | ................ | G03F 7/0045 430/270.1 |
| 2009/0061358 A1* | 3/2009 | Ohashi | ................ | C07J 31/006 430/286.1 |
| 2009/0162788 A1* | 6/2009 | Hada | ................ | C07C 309/17 430/285.1 |
| 2009/0274978 A1* | 11/2009 | Ohashi | ................ | C07J 9/00 430/285.1 |
| 2011/0217654 A1* | 9/2011 | Yamato | ................ | C07C 271/24 430/270.1 |
| 2013/0337382 A1* | 12/2013 | Utsumi | ................ | C07D 333/46 430/285.1 |
| 2014/0322652 A1* | 10/2014 | Komuro | ................ | G03F 7/0397 430/283.1 |
| 2014/0356787 A1* | 12/2014 | Komuro | ................ | C07C 381/12 430/281.1 |
| 2014/0363770 A1* | 12/2014 | Oikawa | ................ | G03F 7/038 430/285.1 |
| 2014/0363772 A1* | 12/2014 | Tsuchiya | ................ | G03F 7/038 430/325 |

FOREIGN PATENT DOCUMENTS

JP 2014-115386 A 6/2014

* cited by examiner

*Primary Examiner* — Martin Angebranndt
(74) *Attorney, Agent, or Firm* — Knobbe Martens Olson & Bear LLP

(57) ABSTRACT

A resist composition which generates acid upon exposure and exhibits changed solubility in a developing solution under action of acid, and which includes a base component (A) which exhibits changed solubility in a developing solution under action of acid and an acid-generator component (B) which generates acid upon exposure, the acid-generator component (B) including a compound (B0-1) represented by general formula (b0) shown below (in the formula, $Yx^{01}$ represents a divalent linking group; n represents an integer of 1 to 3; and $M'^{m+}$ represents an organic cation having a valency of m.

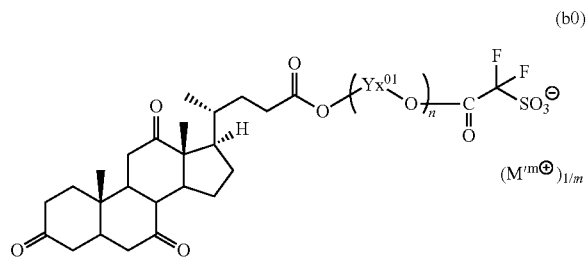

(b0)

8 Claims, No Drawings

RESIST COMPOSITION, METHOD FOR FORMING RESIST PATTERN, ACID GENERATOR AND COMPOUND

RELATED APPLICATIONS

This application claims priority to Japanese Patent Application No. 2015-058676, filed Mar. 20, 2015, the content of which is incorporated herein by reference.

TECHNICAL FIELD

The present invention relates to a resist composition, a method of forming a resist pattern, an acid generator and a compound.

DESCRIPTION OF RELATED ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam, extreme ultraviolet radiation (EUV), and X ray.

A general resist composition contains an acid generator, and the solubility thereof in a developing solution is changed by the action of acid generated from the acid generator. The behavior of acid generated from an acid generator has a large influence on the lithography properties, and various studies have been made related to acid generators. For example, Patent Literature 1 discloses a resist composition adopting an acid generator using a compound having a specific compound structure.

DOCUMENTS OF RELATED ART

Patent Literature

[Patent Document 1] Japanese Unexamined Patent Application, First Publication No. 2014-115386

SUMMARY OF THE INVENTION

However, in the invention described in Patent Literature 1, there was still room for further improvement of lithography properties.

The present invention takes the above circumstances into consideration, with an object of providing a resist composition which exhibits excellent lithography properties, and a method of forming a resist pattern using the resist composition.

A first aspect of the present invention is a resist composition which generates acid upon exposure and exhibits changed solubility in a developing solution under action of acid, and which includes a base component (A) which exhibits changed solubility in a developing solution under action of acid and an acid-generator component (B) which generates acid upon exposure, the acid-generator component (B) including a compound (B0-1) represented by general formula (b0) shown below.

[Chemical Formula 1]

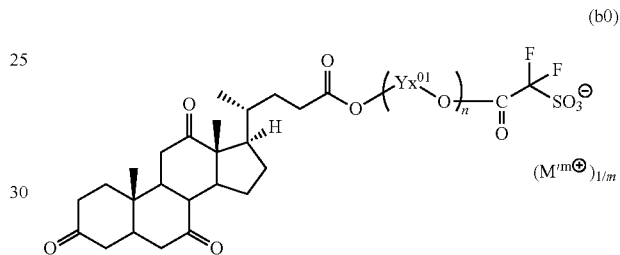

(b0)

In the formula, $Yx^{01}$ represents a divalent linking group; n represents an integer of 1 to 3; and $M'^{m+}$ represents an organic cation having a valency of m.

A second aspect of the present invention is a method of forming a resist pattern, including: using a resist composition according to the first aspect to form a resist film on a substrate, exposing the resist film, and developing the resist film to form a resist pattern.

A third aspect of the present invention is an acid generator containing a compound (B0-1) represented by general formula (b0) shown below.

[Chemical Formula 2]

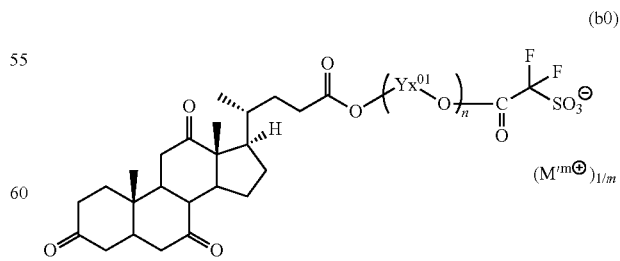

(b0)

In the formula, $Yx^{01}$ represents a divalent linking group; n represents an integer of 1 to 3; and $M'^{m+}$ represents an organic cation having a valency of m.

A fourth aspect of the present invention is a compound represented by general formula (b0) shown below.

[Chemical Formula 3]

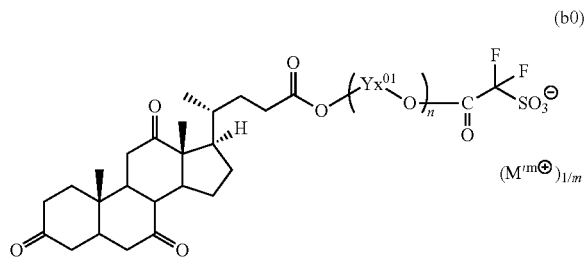

(b0)

In the formula, $Yx^{01}$ represents a divalent linking group; n represents an integer of 1 to 3; and $M'^{m+}$ represents an organic cation having a valency of m.

According to the present invention, there are provided a resist composition which exhibits excellent lithography properties, and a method of forming a resist pattern using the resist composition.

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified.

The term "alkylene group" includes linear, branched or cyclic, divalent saturated hydrocarbon, unless otherwise specified. The same applies for the alkyl group within an alkoxy group.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with a fluorine atom.

The term "structural unit" refers to a monomer unit that contributes to the formation of a polymeric compound (resin, polymer, copolymer).

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid ($CH_2=CH-COOH$) has been substituted with an organic group.

The acrylate ester may have the hydrogen atom bonded to the carbon atom on the α-position substituted with a substituent. The substituent ($R^\alpha$) with which the hydrogen atom bonded to the carbon atom at the α-position is substituted is an atom other than the hydrogen atom or a group, and examples thereof include an alkyl group having from 1 to 5 carbon atoms, a halogenated alkyl group having from 1 to 5 carbon atoms, and a hydroxyalkyl group. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

A "structural unit derived from a hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and may have the hydrogen atom on the α-position substituted with a substituent; and benzoic acid which has a substituent other than a hydroxy group and a carboxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

A "styrene derivative" refers to a compound in which the hydrogen atom on the α-position of styrene is substituted with a substituent such as an alkyl group, a halogenated alkyl group or the like.

A "structural unit derived from styrene" or "structural unit derived from a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

The case of describing "may have a substituent" includes both of the case where the hydrogen atom (—H) is substituted with a monovalent group and the case where the methylene group (—CH$_2$—) is substituted with a divalent group.

The term "exposure" is used as a general concept that includes irradiation with any form of radiation.

<<Resist Composition>>

A first aspect of the present invention is a resist composition which generates acid upon exposure and exhibits changed solubility in a developing solution under action of acid, and which includes a base component (A) which exhibits changed solubility in a developing solution under action of acid and an acid-generator component (B), the acid-generator component (B) including a compound (B0-1) represented by general formula (b0).

In the present embodiment, the resist composition contains a base component (A) (hereafter, referred to as "base component (A)") which exhibits changed solubility in a developing solution.

When a resist film is formed using the resist composition and the formed resist film is subjected to a selective exposure, acid is generated at exposed portions, and the generated acid acts on the component (A) to change the solubility of the component (A) in a developing solution, whereas the solubility of the component (A) in a developing solution is not changed at unexposed portions, thereby generating difference in solubility in a developing solution between exposed portions and unexposed portions. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition.

In the present embodiment, the resist composition may be either a positive resist composition or a negative resist composition.

Further, in the present embodiment, the resist composition may be applied to an alkali developing process using an alkali developing solution in the developing treatment, or a solvent developing process using a developing solution containing an organic solvent (organic developing solution) in the developing treatment, and preferably a solvent developing process.

The resist composition usable in forming a resist pattern has a function of generating acid upon exposure, and in the resist composition, the component (A) may generate acid upon exposure, or an additive component other than the component (A) may generate acid upon exposure.

More specifically, in the present embodiment, the resist composition may be a resist composition (1) containing an acid generator component (B) which generates acid upon exposure (hereafter, referred to as "component (B)");

a resist composition (2) in which the component (A) is a component which generates acid upon exposure; or a resist composition (3) in which the component (A) is a component which generates acid upon exposure, and further containing an acid generator component (B).

That is, when the resist composition of the present invention is the aforementioned resist composition (2) or (3), the component (A) is a "base component which generates acid upon exposure and exhibits changed solubility in a developing solution under action of acid". In the case where the component (A) is a base component which generates acid upon exposure and exhibits changed solubility in a developing solution under action of acid, the component (A1) described later is preferably a polymeric compound which generates acid upon exposure and exhibits changed solubility in a developing solution under action of acid. As the polymeric compound, a resin having a structural unit which generates acid upon exposure can be used. As the structural unit which generates acid upon exposure, a conventional structural unit can be used.

In the present embodiment, it is particularly desirable that the resist composition is the aforementioned resist composition (1).

<Component (A)>

In the present invention, the term "base component" refers to an organic compound capable of forming a film, and is preferably an organic compound having a molecular weight of 500 or more. When the organic compound has a molecular weight of 500 or more, the film-forming ability is improved, and a photosensitive resin pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" refers to a polymer having a molecular weight of 1,000 or more.

As the molecular weight of the polymer, the weight average molecular weight in terms of the polystyrene equivalent value determined by gel permeation chromatography (GPC) is used.

As the component (A'), a resin, a low molecular weight compound, or a combination thereof may be used.

The component (A) is a base component which exhibits increased solubility in a developing solution under action of acid.

In the present invention, the component (A) may be a component that generates acid upon exposure.

In the present embodiment, the component (A) preferably contains a polymeric compound (A1) having a structural unit containing an acid decomposable group which exhibits increased polarity by the action of acid (hereafter, referred to as "structural unit (a1)"), a structural unit derived from an acrylate ester containing an —SO$_2$— containing cyclic group, a lactone-containing cyclic group, a carbonate-containing cyclic group or any other heterocyclic group (hereafter, referred to as "structural unit (a2)"), a structural unit containing a polar group-containing aliphatic hydrocarbon group (hereafter, referred to as "structural unit (a3)"), and a structural unit containing an acid non-dissociable cyclic group (hereafter, referred to as "structural unit (a4)").

(Structural Unit (a1))

The structural unit (a1) is a structural unit containing an acid decomposable group that exhibits increased polarity by the action of acid.

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group ($-SO_3H$). Among these, a sulfo group or a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

Here, the "acid dissociable group" includes:

(i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes and, the solubility in an organic developing solution is relatively decreased.

The acid dissociable group is not particularly limited, and any of the groups that have been conventionally proposed as acid dissociable groups for the base resins of chemically amplified resists can be used.

Examples of the acid dissociable group for protecting the carboxy group or hydroxy group as a polar group include the acid dissociable group represented by general formula (a1-r-1) shown below (hereafter, for the sake of convenience, sometimes referred to as "acetal-type acid dissociable group").

[Chemical Formula 4]

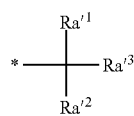

(a1-r-1)

In the formula, $Ra^{r1}$ and $Ra^{r2}$ represents a hydrogen atom or an alkyl group; and $Ra^{r3}$ represents a hydrocarbon group, provided that $Ra^{r3}$ may be bonded to $Ra^{r1}$ or $Ra^{r2}$; and * represents a valence bond.

In formula (a1-r-1), as the lower alkyl group for $Ra^{r1}$ and $Ra^{r2}$, the same lower alkyl groups as those described above the alkyl groups as the substituent which may be bonded to the carbon atom on the α-position of the aforementioned α-substituted alkylester can be used, although a methyl group or ethyl group is preferable, and a methyl group is particularly desirable.

The hydrocarbon group for $Ra^{r3}$ is preferably an alkyl group of 1 to 20 carbon atoms, more preferably an alkyl group of 1 to 10 carbon atoms, and still more preferably a linear or branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, a 1,1-dimethylethyl group, a 1,1-diethylpropyl group, a 2,2-dimethylpropyl group and a 2,2-dimethylbutyl group.

In the case where $Ra^{r3}$ represents a cyclic hydrocarbon group, the cyclic hydrocarbon group may be aliphatic or aromatic, and may be polycyclic or monocyclic. As the monocyclic aliphatic hydrocarbon group, a group in which 1 hydrogen atom has been removed from a monocycloalkane is preferable. The monocycloalkane preferably has 3 to 8 carbon atoms, and specific examples thereof include cyclopentane, cyclohexane and cyclooctane. As the polycyclic group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

In the case where the hydrocarbon group is an aromatic hydrocarbon group, examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which 1 hydrogen atom has been removed from the aforementioned aromatic hydrocarbon ring (aryl group); and a group in which 1 hydrogen atom of the aforementioned aryl group has been substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atom, more preferably 1 or 2, and most preferably 1.

In the case where $Ra^{r3}$ is bonded to $Ra^{r1}$ or $Ra^{r2}$ to form a ring, the cyclic group is preferably a 4 to 7-membered ring, and more preferably a 4 to 6-membered ring. Specific examples of the cyclic group include tetrahydropyranyl group and tetrahydrofuranyl group.

Examples of the acid dissociable group for protecting the carboxy group as a polar group include the acid dissociable group represented by general formula (a1-r-2) shown below (hereafter, with respect to the acid dissociable group represented by the following formula (a1-r-2), the acid dissociable group constituted of alkyl groups is referred to as "tertiary ester-type acid dissociable group").

[Chemical Formula 5]

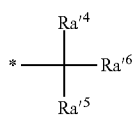

(a1-r-2)

In the formula, $Ra'^4$ to $Ra'^6$ each independently represents a hydrocarbon group, provided that $Ra'^5$ and $Ra'^6$ may be mutually bonded to form a ring; and * represents a valence bond.

As the hydrocarbon group for $Ra'^4$ to $Ra'^6$, the same groups as those described above for $Ra'^3$ can be mentioned. $Ra'^4$ is preferably an alkyl group having from 1 to 5 carbon atoms. In the case where $Ra'^5$ and $Ra'^6$ are mutually bonded to form a ring, a group represented by general formula (a1-r2-1) shown below can be mentioned.

On the other hand, in the case where $Ra'^4$ to $Ra'^6$ are not mutually bonded and independently represent a hydrocarbon group, the group represented by general formula (a1-r2-2) shown below can be mentioned.

[Chemical Formula 6]

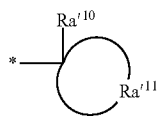

(a1-r2-1)

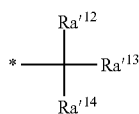

(a1-r2-2)

In the formulae, $Ra'^{10}$ represents an alkyl group of 1 to 10 carbon atoms; $Ra'^{11}$ is a group which forms an aliphatic cyclic group together with a carbon atom having $Ra'^{10}$ bonded thereto; and $Ra'^{12}$ to $Ra'^{14}$ each independently represents a hydrocarbon group; and * represents a valence bond.

In the formula (a1-r2-1), as the alkyl group of 1 to 10 carbon atoms for $Ra'^{10}$, the same groups as described above for the linear or branched alkyl group for $Ra'^3$ in the formula (a1-r-1) are preferable. In the formula (a1-r2-1), as the aliphatic cyclic group which is formed by $Ra'^{11}$, the same groups as those described above for the cyclic alkyl group for $Ra'^3$ in the formula (a1-r-1) are preferable.

In the formula (a1-r2-2), it is preferable that $Ra'^{12}$ and $Ra'^{14}$ each independently represents an alkyl group or 1 to 10 carbon atoms, and it is more preferable that the alkyl group is the same group as the described above for the linear or branched alkyl group for $Ra'^3$ in the formula (a1-r-1), it is still more preferable that the alkyl group is a linear alkyl group of 1 to 5 carbon atoms, and it is particularly preferable that the alkyl group is a methyl group or an ethyl group.

In the formula (a1-r2-2), it is preferable that $Ra'^{13}$ is the same group as described above for the linear, branched or cyclic alkyl group for $Ra'^3$ in the formula (a1-r-1).

Among these, the same cyclic alkyl group as those describe above for $Ra'^3$ is more preferable.

Specific examples of the formula (a1-r2-1) are shown below. In the formulae shown below, "*" represents a valence bond.

[Chemical Formula 7]

(r-pr-m1)

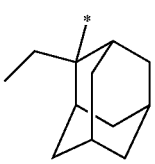

(r-pr-m2)

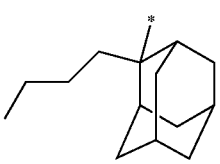

(r-pr-m3)

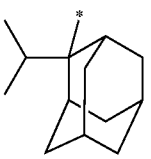

(r-pr-m4)

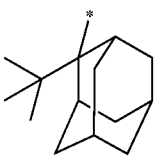

(r-pr-m5)

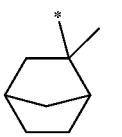

(r-pr-m6)

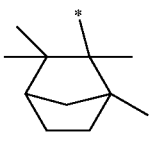

(r-pr-m7)

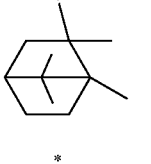

(r-pr-m8)

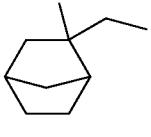

(r-pr-m9)

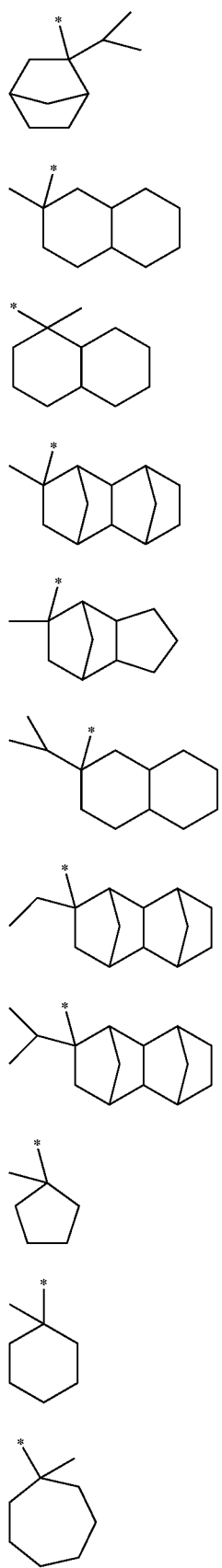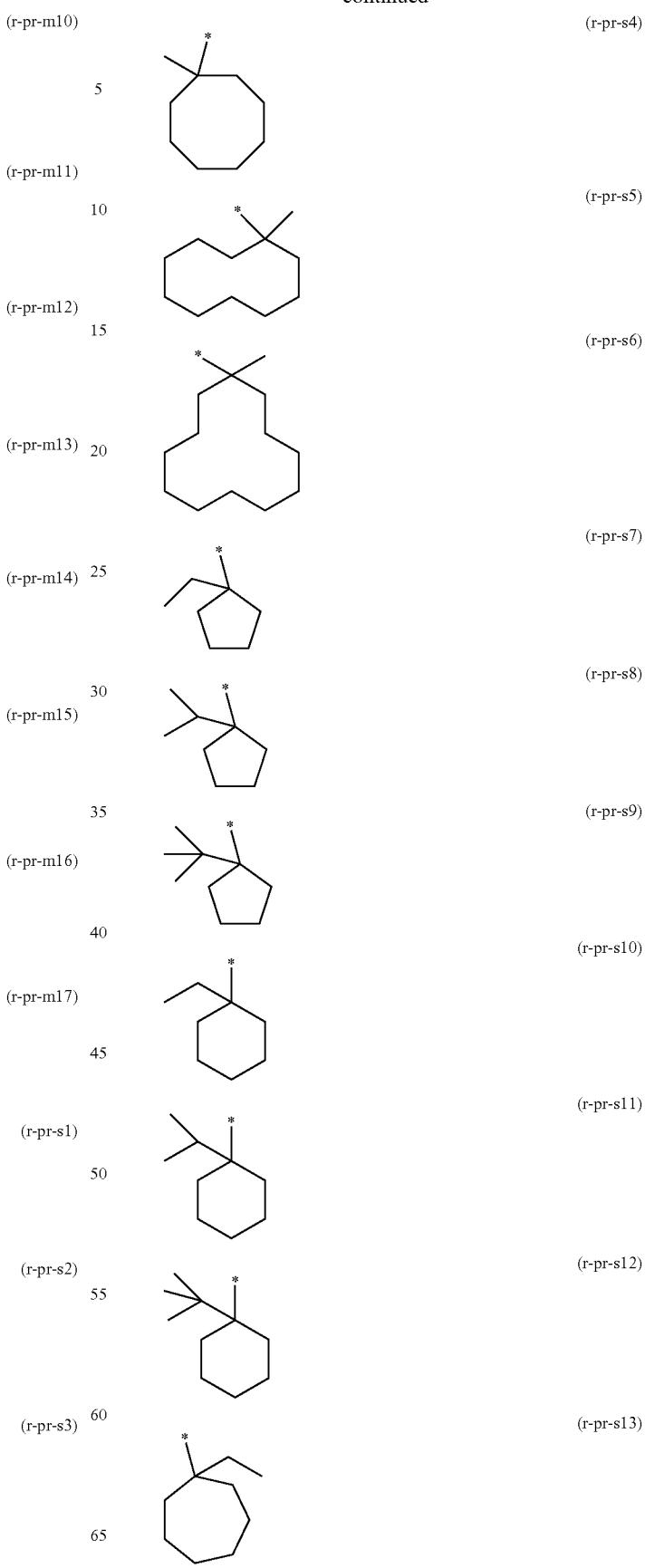

(r-pr-s14)
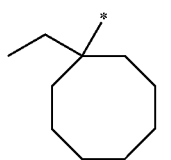
(r-pr-s15)
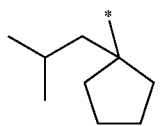
(r-pr-s16)
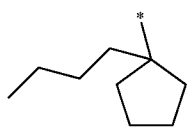
(r-pr-s17)
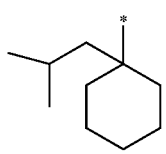
(r-pr-s18)
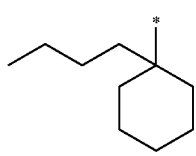
Specific examples of the formula (a1-r2-2) are shown below.
[Chemical Formula 8]
(r-pr-cm1)
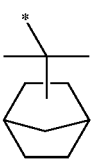
(r-pr-cm2)
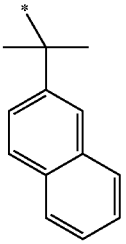
(r-pr-cm3)
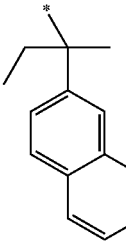
(r-pr-cm4)
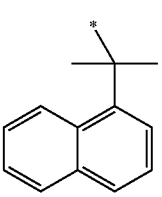
(r-pr-cm5)
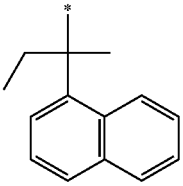
(r-pr-cm6)
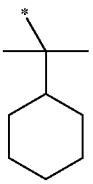
(r-pr-cm7)
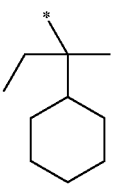
(r-pr-cm8)
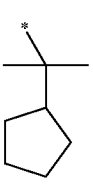
(r-pr-cs1)
(r-pr-cs2)
(r-pr-cs3)

-continued

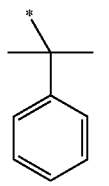
(r-pr-cs4)

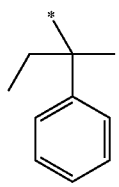
(r-pr-cs5)

(r-pr-c1)

(r-pr-c2)

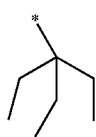
(r-pr-c3)

Examples of the acid dissociable group for protecting a hydroxy group as a polar group include the acid dissociable group represented by general formula (a1-r-3) shown below (hereafter, referred to as "tertiary alkyloxycarbonyl-type acid dissociable group").

[Chemical Formula 9]

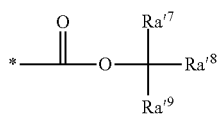
(a1-r-3)

In the formula, $Ra'^7$ to $Ra'^9$ each independently represents an alkyl group; and * represents a valence bond.

In the formula (a1-r-3), $Ra'^7$ to $Ra'^9$ is preferably an alkyl group of 1 to 5 carbon atoms, and more preferably an alkyl group of 1 to 3 carbon atoms.

Further, the total number of carbon atoms within the alkyl group is preferably 3 to 7, more preferably 3 to 5, and most preferably 3 or 4.

Examples of the structural unit (a1) include a structural unit derived from an acrylate ester which may have the hydrogen atom bonded to the carbon atom on the α-position substituted with a substituent and contains an acid decomposable group which exhibits increased polarity by the action of acid; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinyl-benzoic acid derivative in which at least a part of the hydrogen atom within —C(═O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

As the structural unit (a1), structural units represented by general formula (a1-1) or (a1-2) shown below are preferable.

[Chemical Formula 10]

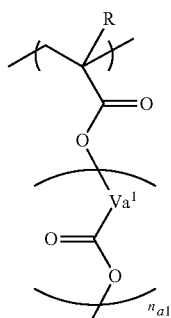
(a1-1)

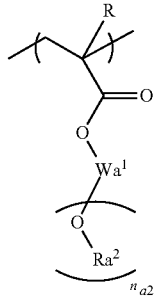
(a1-2)

In the formulae, R represents a hydrogen atom, an alkyl group of 1 to 5 carbon atoms or a halogenated alkyl group of 1 to 5 carbon atoms; $Va^1$ represents a divalent hydrocarbon group which may contain an ether bond, an urethane bond or an amide bond; each $n_{a1}$ represents an integer of 0 to 2; $Ra^1$ represents an acid dissociable group represented by the aforementioned formula (a1-r-1) or (a1-r-2); $Wa^1$ represents a hydrocarbon group having a valency of $n_{a2}+1$; $n_{a2}$ represents an integer of 1 to 3; and $Ra^2$ represents an acid dissociable group represented by the aforementioned formula (a1-r-1) or (a1-r-3).

In general formula (a1-1), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

The hydrocarbon group for $Va^1$ may be either an aliphatic hydrocarbon group or an aromatic hydrocarbon group. An "aliphatic hydrocarbon group" refers to a hydrocarbon group that has no aromaticity. The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

Further, as the group for $Va^1$, a group in which the aforementioned divalent hydrocarbon group has been bonded via an ether bond, urethane bond or amide bond can be mentioned.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)_2CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group is a hydrocarbon group having an aromatic ring.

The aromatic hydrocarbon group as the divalent hydrocarbon group for $Va^1$ preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

In the aforementioned formula (a1-2), the hydrocarbon group for $Wa^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the specific examples thereof, the same groups as those described above for $Va^1$ in the aforementioned formula (a1-1) can be mentioned.

The valency of $n_{a2}+1$ is preferably divalent, trivalent or tetravalent, and divalent or trivalent is more preferable.

As the structural unit (a1-2), a structural unit represented by general formula (a1-2-01) shown below is particularly desirable.

[Chemical Formula 11]

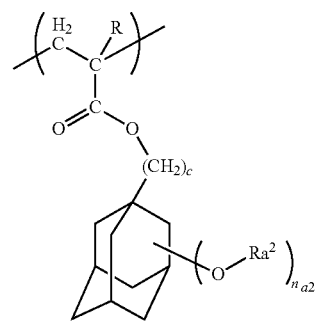

(a1-2-01)

In the formula (a1-2-01), $Ra^2$ represents an acid dissociable group represented by the aforementioned formula (a1-r-1) or (a1-r-3); $n_{a2}$ is an integer of 1 to 3, preferably 1 or 2, and more preferably 1; c is an integer of 0 to 3, preferably 0 or 1, and more preferably 1; R is the same as defined above.
Specific examples of the structural units (a1-1) and (a1-2) are shown below. In the formulae shown below, $R^\alpha$ represents a hydrogen atom, a methyl group or a trifluoromethyl group.
[Chemical Formula 12]
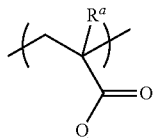
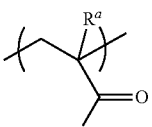
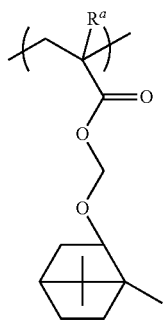
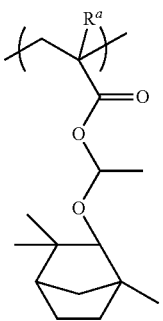
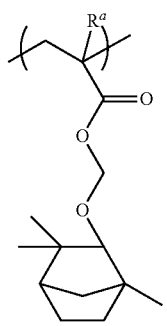
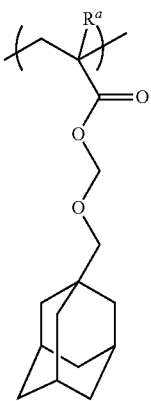
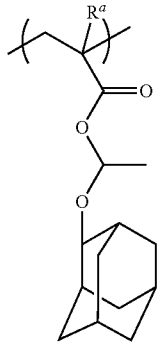
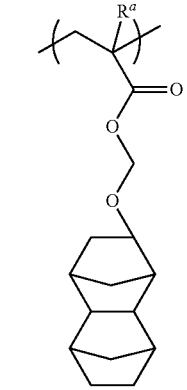
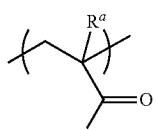
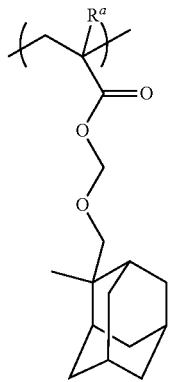
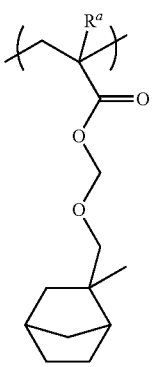
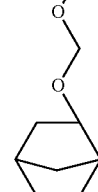
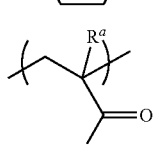
[Chemical Formula 13]
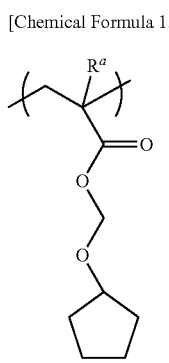
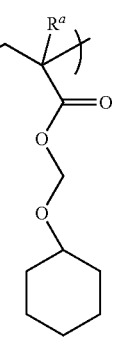

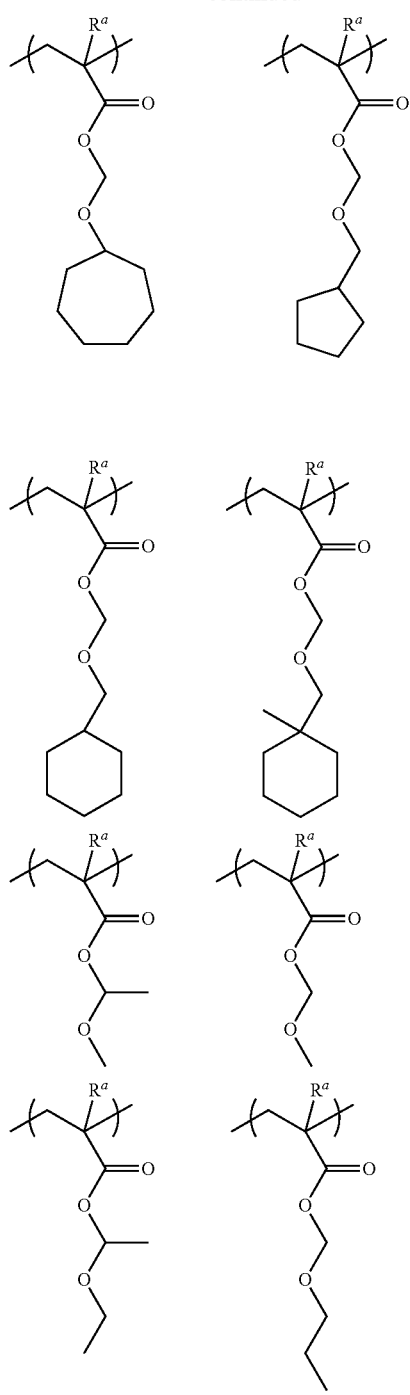
[Chemical Formula 14]
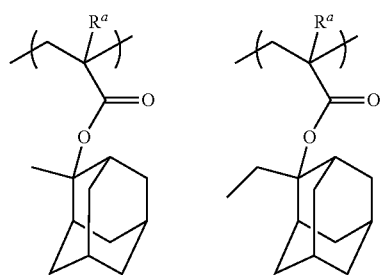
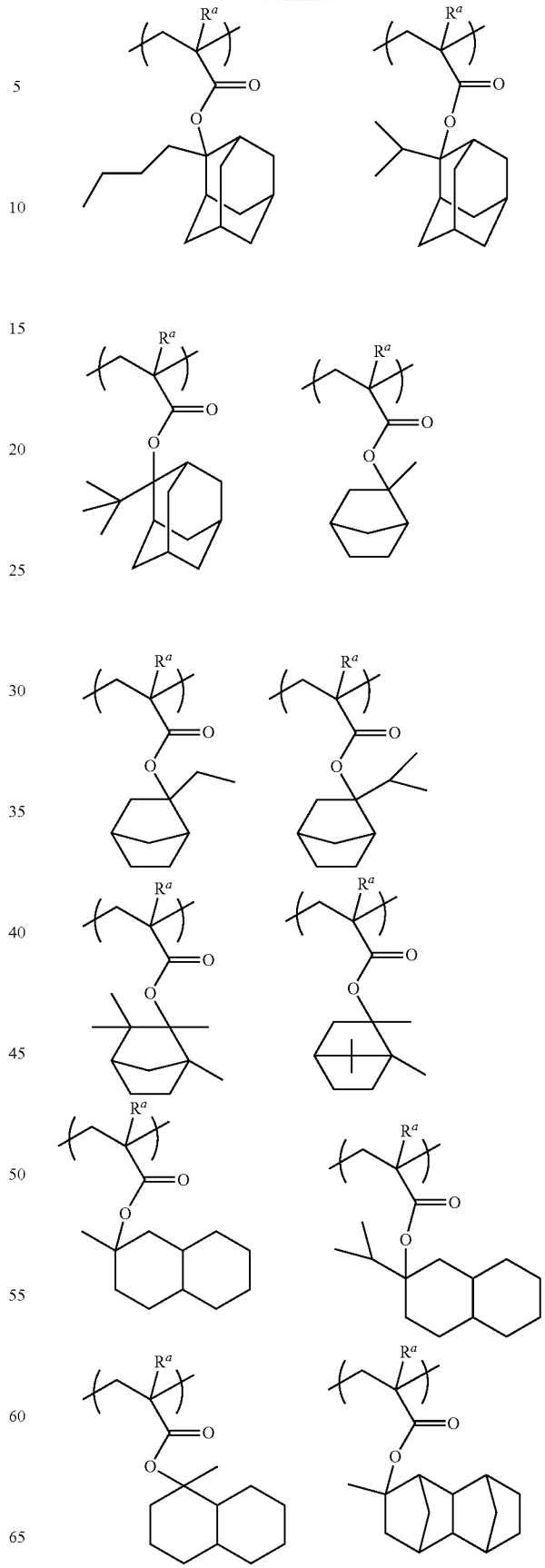

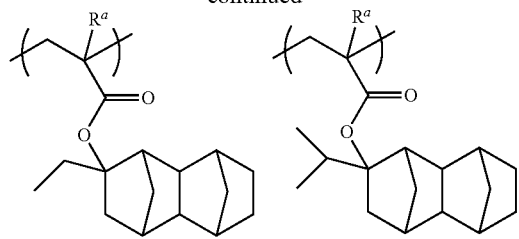
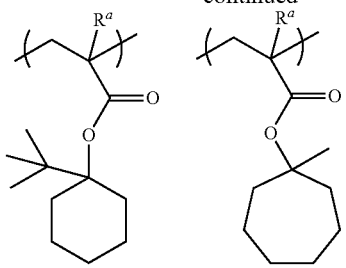
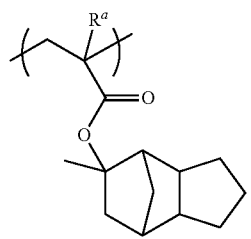
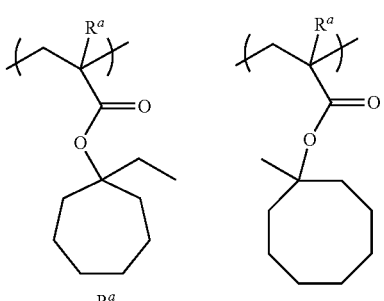
[Chemical Formula 15]
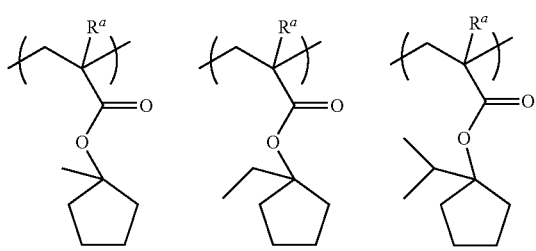
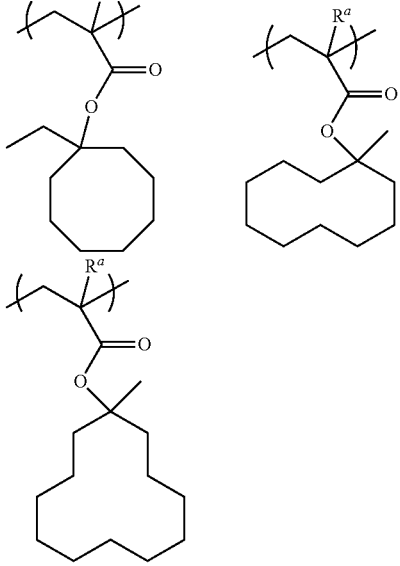
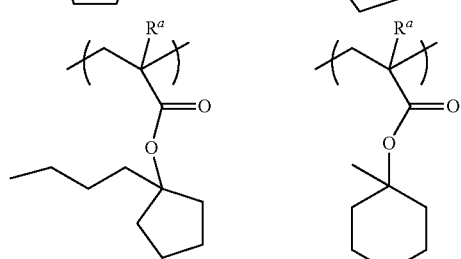
[Chemical Formula 16]
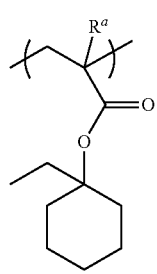
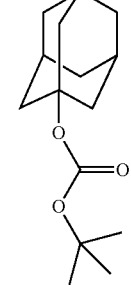
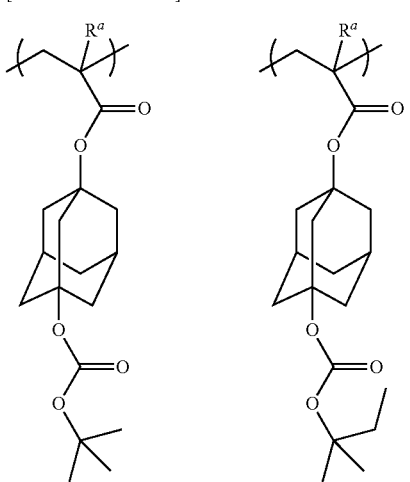

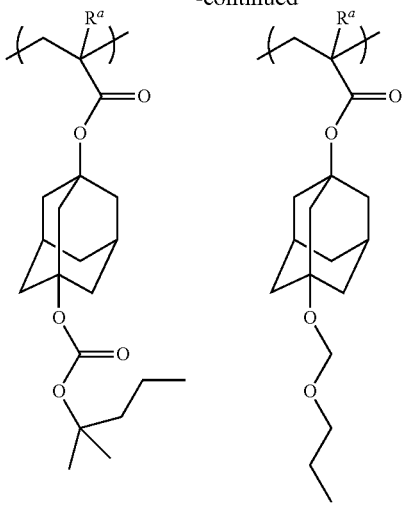
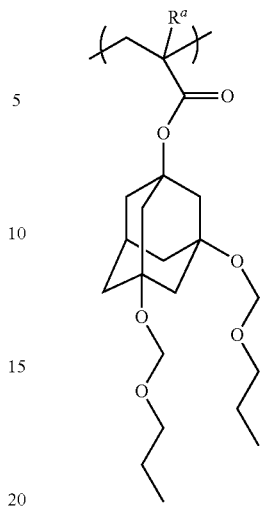
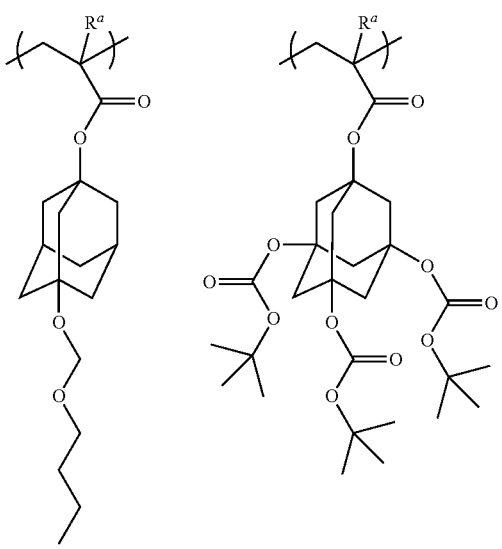
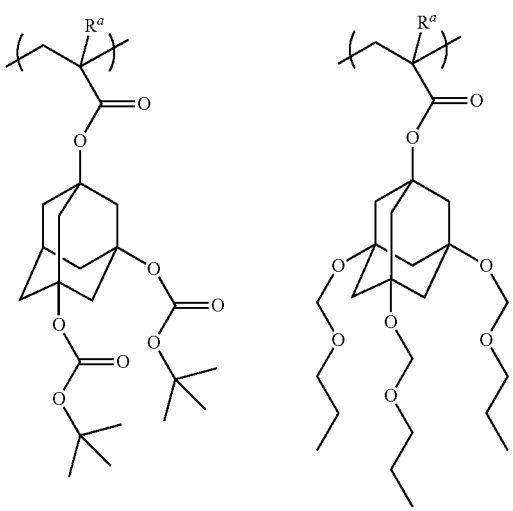
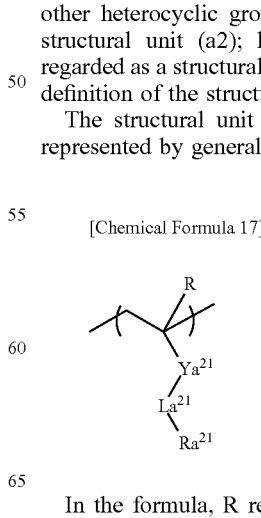

In the component (A), the amount of the structural unit (a1) based on the combined total of all structural units constituting the component (A) is preferably 20 to 80 mol %, more preferably 20 to 75 mol %, and still more preferably 25 to 70 mol %. By ensuring the lower limit, various lithography properties such as sensitivity, resolution and LWR are improved. On the other hand, when the amount of the structural unit (a1) is no more than the upper limit of the above-mentioned range, a good balance can be achieved with the other structural units.

(Structural Unit (a2))

In the present embodiment, the base component preferably contains a structural unit (a2) having an —$SO_2$— containing cyclic group, a lactone-containing cyclic group, a carbonate-containing cyclic group or any other heterocyclic group.

When the component (A) is used for forming a resist film, the structural unit (a2) containing an —$SO_2$— containing cyclic group, a lactone-containing cyclic group, a carbonate-containing cyclic group or any other heterocyclic group is effective in improving the adhesion between the resist film and the substrate.

A structural unit (a1) (described later) which contains an —$SO_2$— containing cyclic group, a lactone-containing cyclic group, a carbonate-containing cyclic group or any other heterocyclic group falls under the definition of the structural unit (a2); however, such a structural unit is regarded as a structural unit (a1), and does not fall under the definition of the structural unit (a2).

The structural unit (a2) is preferably a structural unit represented by general formula (a2-1) shown below.

[Chemical Formula 17]

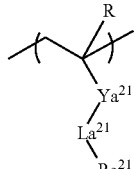

(a2-1)

In the formula, R represents a hydrogen atom, an alkyl group of 1 to 5 carbon atoms, a halogenated alkyl group of 1 to 5 carbon atoms, a hydroxyalkyl group, an alkoxy group; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group, provided that, when $La^{21}$ represents —O—, $Ya^{21}$ does not represents —CO—; and $Ra^{21}$ represents an —$SO_2$— containing cyclic group, a lactone-containing cyclic group, a carbonate-containing cyclic group or any other heterocyclic group.

In formula (a2-1), $Ra^{21}$ represents an —$SO_2$— containing cyclic group, a lactone-containing cyclic group, a heterocyclic group or a carbonate-containing cyclic group.

An "—$SO_2$— containing cyclic group" refers to a cyclic group having a ring containing —$SO_2$— within the ring structure thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable. More specific examples of the —$SO_2$— containing cyclic group include groups represented by general formulas (a5-r-1) to (a5-r-4) shown below.

[Chemical Formula 18]

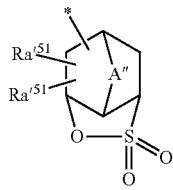
(a5-r-1)

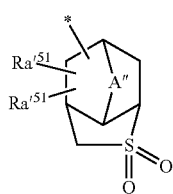
(a5-r-2)

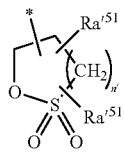
(a5-r-3)

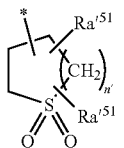
(a5-r-4)

In the formulae, each $Ra'^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group of 1 to 5 carbon atoms which may contain an oxygen atom or a sulfur atom; and n' represents an integer of 0 to 2.

In general formulae (a5-r-1) to (a5-r-4), A" is the same as defined for A" in general formulae (a2-r-1) to (a2-r-7) described later. The alkyl group, alkoxy group, halogen atom, halogenated alkyl group, —COOR", —OC(=O)R" and hydroxyalkyl group for $Ra'^{51}$ are the same as defined for $Ra^{21}$ in general formulae (a2-r-1) to (a2-r-7) described later.

Specific examples of the groups represented by the aforementioned general formulae (a5-r-1) to (a5-r-4) are shown below. In the formulae shown below, "Ac" represents an acetyl group.

[Chemical Formula 19]

(r-sl-1-1)

(r-sl-1-2)

(r-sl-1-3)

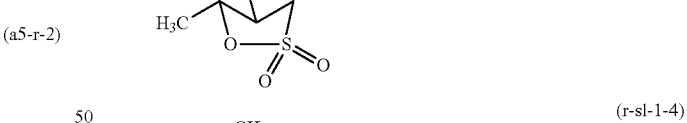
(r-sl-1-4)

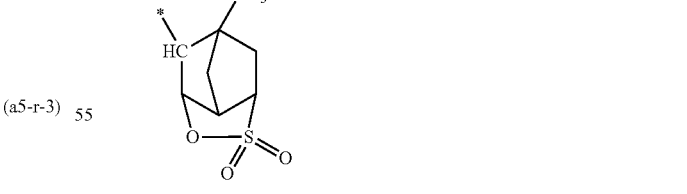
(r-sl-1-5)

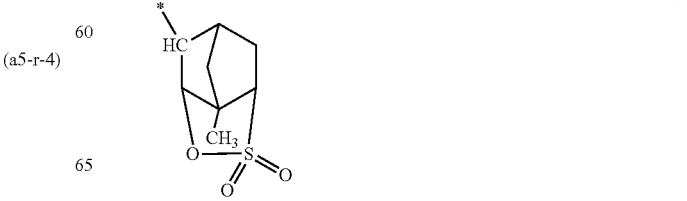

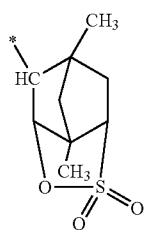 (r-sl-1-6)
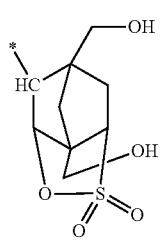 (r-sl-1-7)
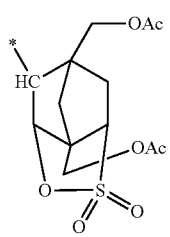 (r-sl-1-8)
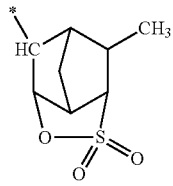 (r-sl-1-9)
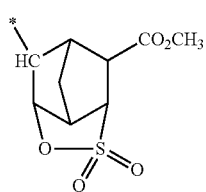 (r-sl-1-10)
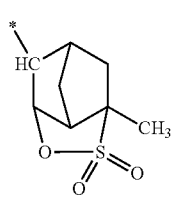 (r-sl-1-11)
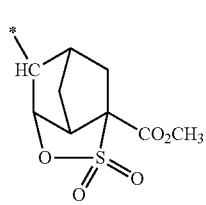 (r-sl-1-12)
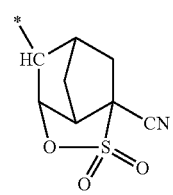 (r-sl-1-13)
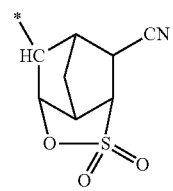 (r-sl-1-14)
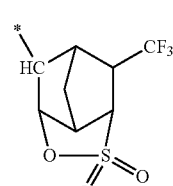 (r-sl-1-15)
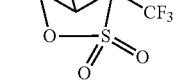 (r-sl-1-16)
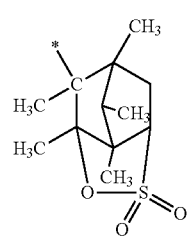 (r-sl-1-17)
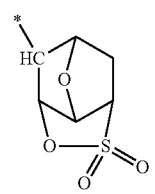 (r-sl-1-18)
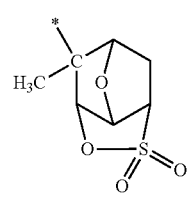 (r-sl-1-19)
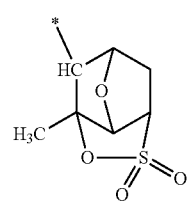 (r-sl-1-20)

(r-sl-1-21)
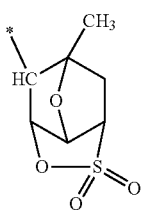
[Chemical Formula 20]
(r-sl-1-22)
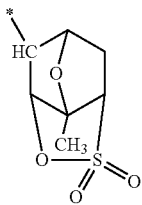
(r-sl-1-23)
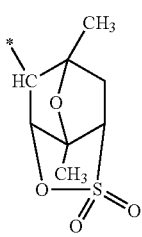
(r-sl-1-24)
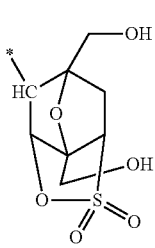
(r-sl-1-25)
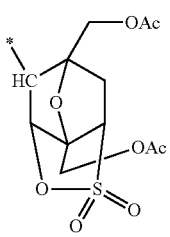
(r-sl-1-26)
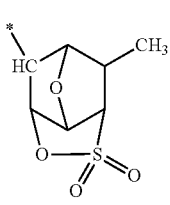
(r-sl-1-27)
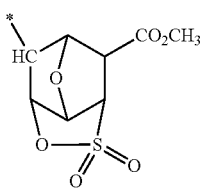
(r-sl-1-28)
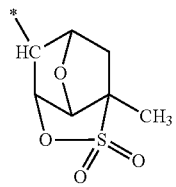
(r-sl-1-29)
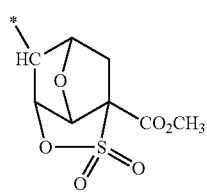
(r-sl-1-30)
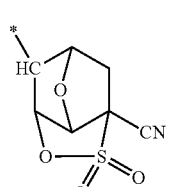
(r-sl-1-31)
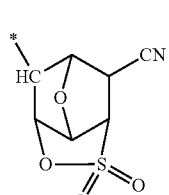
(r-sl-1-32)
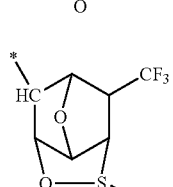
(r-sl-1-33)
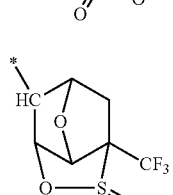
[Chemical Formula 21]
(r-sl-2-1)
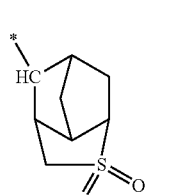
(r-sl-2-2)
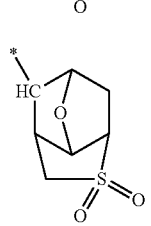

-continued (r-sl-3-1)

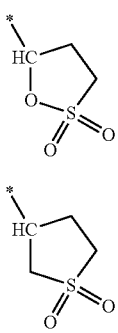

(r-sl-4-1)

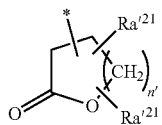

In the present embodiment, when the structural unit (a2) contains an —$SO_2$— containing cyclic group, there is no particular limitation as long as the acrylate ester monomer containing an —$SO_2$— containing cyclic group has a log P value of less than 1.2. Among these, a group represented by the aforementioned general formula (a5-r-1) is preferable, at least one member selected from the group consisting of groups represented by the aforementioned chemical formulas (r-sl-1-1), (r-sl-1-18), (r-sl-3-1) and (r-sl-4-1) is more preferable, and a group represented by chemical formula (r-sl-1-1) is most preferable.

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

As the lactone-containing cyclic group, there is no particular limitation, and an arbitrary group may be used.

Specific examples include groups represented by general formulae (a2-r-1) to (a2-r-7) shown below. Hereinbelow, "*" represents a valence bond.

[Chemical Formula 22]

(a2-r-1)

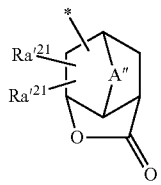

(a2-r-2)

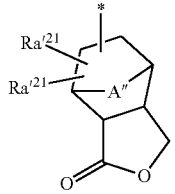

(a2-r-3)

(a2-r-4)

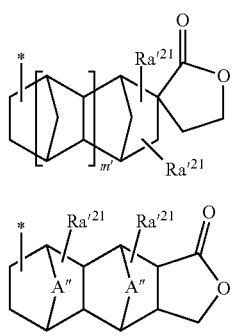

(a2-r-5)

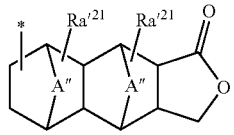

(a2-r-6)

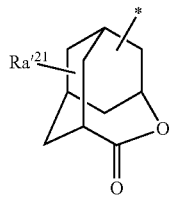

(a2-r-7)

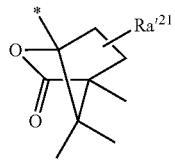

In the formulae, each $Ra'^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group of 1 to 5 carbon atoms which may contain an oxygen atom or a sulfur atom; n' represents an integer of 0 to 2; and m' represents 0 or 1.

In general formulae (a2-r-1) to (a2-r-7) above, A" represents an oxygen atom (—O—), a sulfur atom (—S—) or an alkylene group of 1 to 5 carbon atoms which may contain an oxygen atom or a sulfur atom. As the alkylene group of 1 to 5 carbon atoms for A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—$CH_2$—, —$CH_2$—O—$CH_2$—, —S—$CH_2$— and —$CH_2$—S—$CH_2$—. As A", an alkylene group of 1 to 5 carbon atoms or —O— is preferable, more preferably an alkylene group of 1 to 5 carbon atoms, and most preferably a methylene group. Each $Ra'^{21}$ independently represents an alkyl group, an alkoxy group, a halogen atom, a halogenated alkyl group, —COOR", —OC(=O)R", a hydroxyalkyl group or a cyano group.

The alkyl group for $Ra'^{21}$ is preferably an alkyl group of 1 to 5 carbon atoms.

The alkoxy group for $Ra'^{21}$ is preferably an alkoxy group of 1 to 6 carbon atoms.

Further, the alkoxy group is preferably a linear or branched alkoxy group. Specific examples of the alkoxy groups include the aforementioned alkyl groups for Ra'$^{21}$ having an oxygen atom (—O—) bonded thereto.

As examples of the halogen atom for Ra'$^{21}$, a fluorine atom, chlorine atom, bromine atom and iodine atom can be given. Among these, a fluorine atom is preferable.

Examples of the halogenated alkyl group for Ra'$^{21}$ include groups in which part or all of the hydrogen atoms within the aforementioned alkyl group for Ra'$^{21}$ has been substituted with the aforementioned halogen atoms. As the halogenated alkyl group, a fluorinated alkyl group is preferable, and a perfluoroalkyl group is particularly desirable.

Specific examples of the groups represented by the aforementioned general formulae (a2-r-1) to (a2-r-7) are shown below.

[Chemical Formula 23]

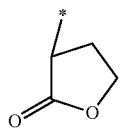
(r-lc-1-1)

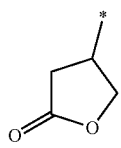
(r-lc-1-2)

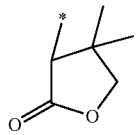
(r-lc-1-3)

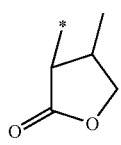
(r-lc-1-4)

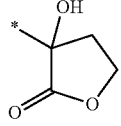
(r-lc-1-5)

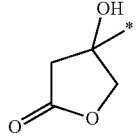
(r-lc-1-6)

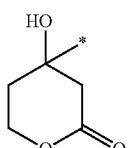
(r-lc-1-7)

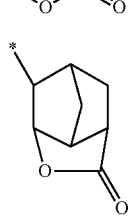
(r-lc-2-1)

-continued

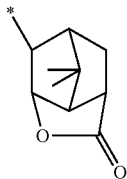
(r-lc-2-2)

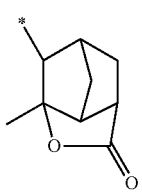
(r-lc-2-3)

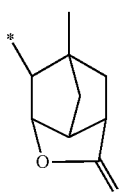
(r-lc-2-4)

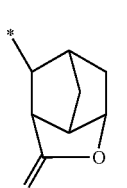
(r-lc-2-5)

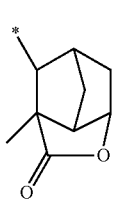
(r-lc-2-6)

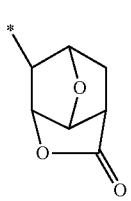
(r-lc-2-7)

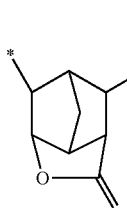
(r-lc-2-8)

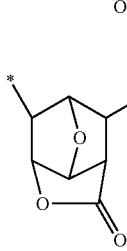
(r-lc-2-9)

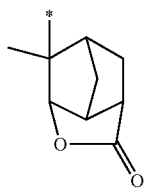 (r-lc-2-10)
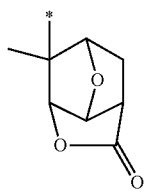 (r-lc-2-11)
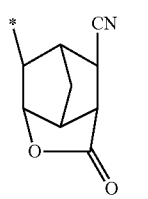 (r-lc-2-12)
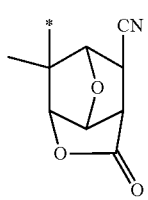 (r-lc-2-13)
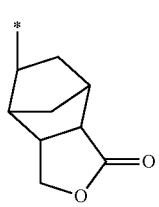 (r-lc-3-1)
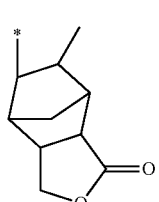 (r-lc-3-2)
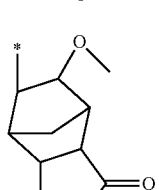 (r-lc-3-3)
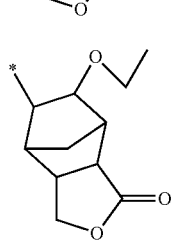 (r-lc-3-4)
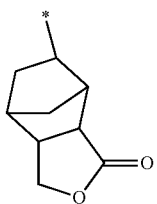 (r-lc-3-5)
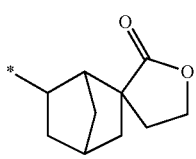 (r-lc-4-1)
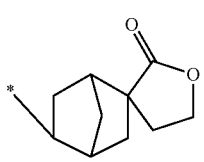 (r-lc-4-2)
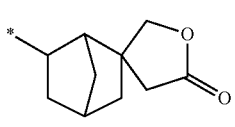 (r-lc-4-3)
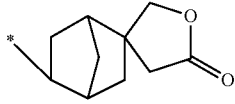 (r-lc-4-4)
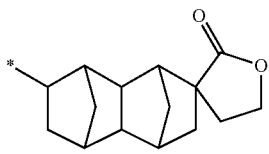 (r-lc-4-5)
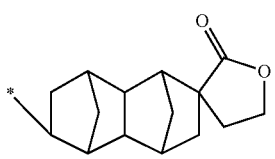 (r-lc-4-6)
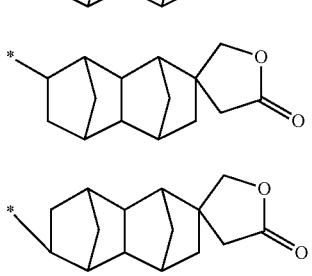 (r-lc-4-7)
(r-lc-4-8)
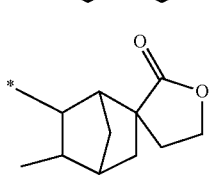 (r-lc-4-9)

-continued

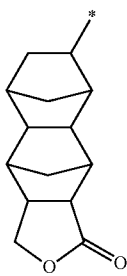 (r-lc-5-1)

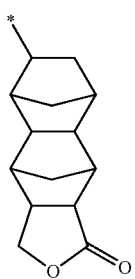 (r-lc-5-2)

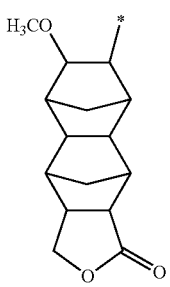 (r-lc-5-3)

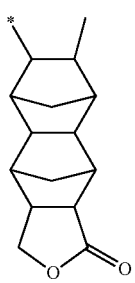 (r-lc-5-4)

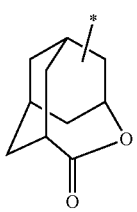 (r-lc-6-1)

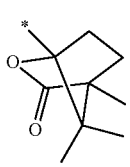 (r-lc-7-1)

In the present embodiment, the structural unit (a2) preferably has a group represented by the aforementioned formula (a2-r-1) or (a2-r-2), and more preferably a group represented by the aforementioned chemical formula (r-lc-1-1) or (r-lc-2-7).

The term "carbonate-containing cyclic group" refers to a cyclic group including a ring containing a —O—C(=O)—O— structure (carbonate ring). The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group as the cyclic hydrocarbon group for $R^1$ is not particularly limited, and an arbitrary group may be used. Specific examples include groups represented by general formulas (ax3-r-1) to (ax3-r-3) shown below.

[Chemical Formula 24]

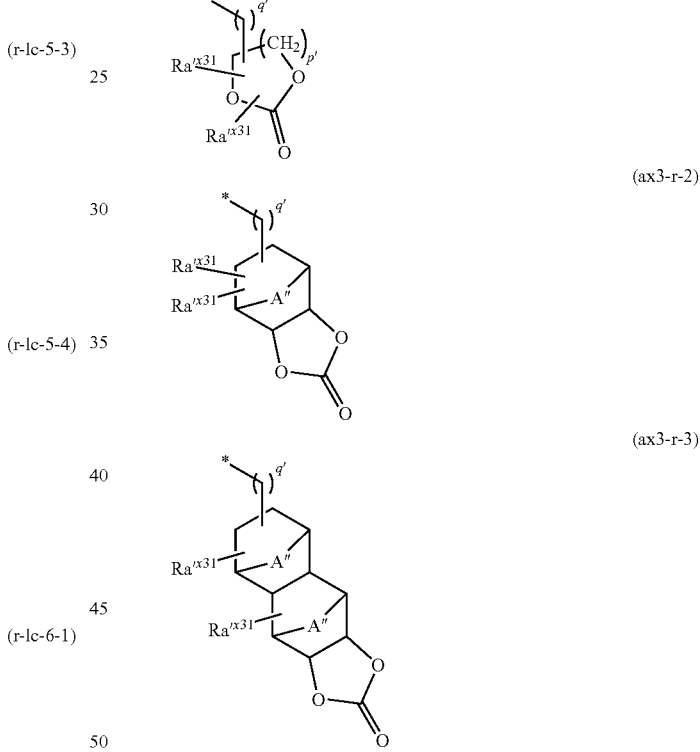

In the formulae, each $Ra'^{x31}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group of 1 to 5 carbon atoms which may contain an oxygen atom or a sulfur atom; and q' represents 0 or 1.

In general formulae (ax3-r-1) to (ax3-r-3), A" is the same as defined for A" in general formula (a2-r-1).

Examples of the alkyl group, alkoxy group, halogen atom, halogenated alkyl group, —COOR", —OC(=O)R" and hydroxyalkyl group for $Ra'^{31}$ include the same groups as those described above in the explanation of $Ra'^{21}$ in the general formulas (a2-r-1) to (a2-r-7).

Specific examples of the groups represented by the aforementioned general formulae (ax3-r-1) to (ax3-r-3) are shown below.
[Chemical Formula 25]
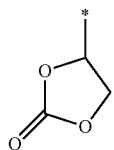 (r-cr-1-1)
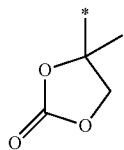 (r-cr-1-2)
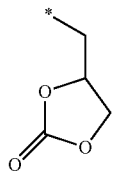 (r-cr-1-3)
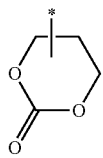 (r-cr-1-4)
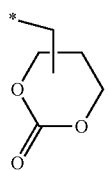 (r-cr-1-5)
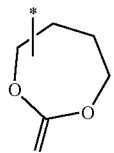 (r-cr-1-6)
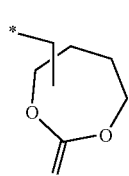 (r-cr-1-6)
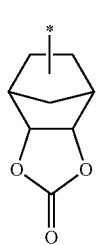 (r-cr-2-1)
-continued
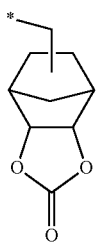 (r-cr-2-2)
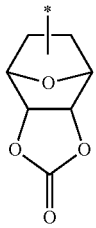 (r-cr-2-3)
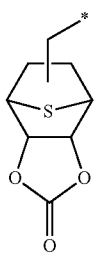 (r-cr-2-4)
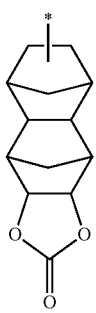 (r-cr-3-1)
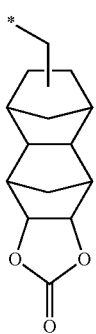 (r-cr-3-2)

-continued (r-cr-3-3)

(r-cr-3-4)
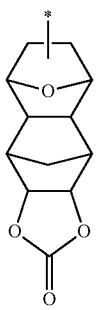

(r-cr-3-5)
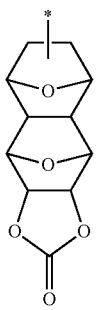

A "heterocyclic group" refers to a cyclic group containing, in addition to carbon, 1 or more atoms other than carbon. Examples of the heterocyclic group include heterocyclic groups represented by the aforementioned formulae (r-hr-1) to (r-hr-16) and nitrogen-containing heterocyclic groups. Examples of the nitrogen-containing heterocyclic groups include cycloalkyl groups of 3 to 8 carbon atoms which may be substituted with 1 or 2 oxo groups. Preferable examples of the cycloalkyl group include 2,5-dioxopyrrolidine and 2,6-dioxopiperidine.

[Chemical Formula 26]

(r-hr-1)
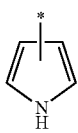

(r-hr-2)
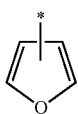

(r-hr-3)
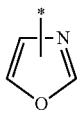

(r-hr-4)
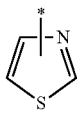

(r-hr-5)
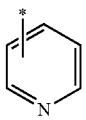

(r-hr-6)
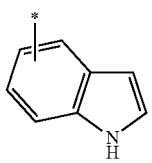

(r-hr-7)
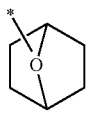

(r-hr-8)
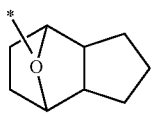

(r-hr-9)

(r-hr-10)
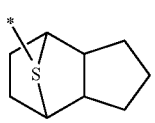

(r-hr-11)

(r-hr-12)
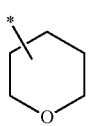

(r-hr-13)

(r-hr-14)
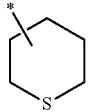

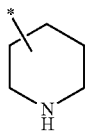
(r-hr-15)

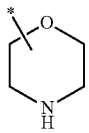
(r-hr-16)

As the structural unit (a2) contained in the component (A1), 1 type of structural unit may be used, or 2 or more types may be used.

When the component (A1) contains the structural unit (a2), the amount of the structural unit (a2) based on the combined total of all structural units constituting the component (A) is preferably 1 to 80 mol %, more preferably 5 to 70 mol %, still more preferably 10 to 65 mol %, and most preferably 10 to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties and pattern shape can be improved.

(Structural Unit (a3))

The structural unit (a3) is a structural unit containing a polar group-containing aliphatic hydrocarbon group (provided that the structural units that fall under the definition of structural units (a1) and (a2) are excluded).

When the component (A1) includes the structural unit (a3), it is presumed that the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 27]

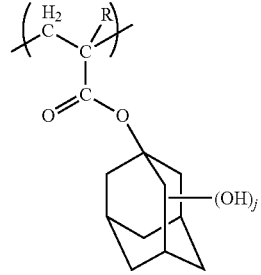
(a3-1)

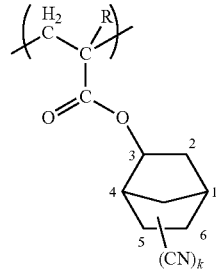
(a3-2)

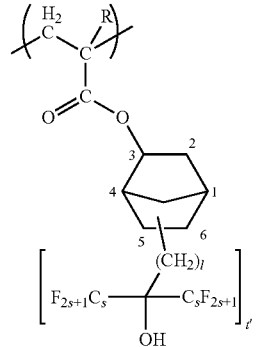
(a3-3)

In the formulas, R is the same as defined above; j is an integer of 1 to 3; k is an integer of 1 to 3; t' is an integer of 1 to 3; 1 is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 type of structural unit may be used, or 2 or more types may be used.

The amount of the structural unit (a3) within the component (A1) based on the combined total of all structural units constituting the component (A1) is preferably 5 to 50 mol %, more preferably 5 to 40 mol %, and still more preferably 5 to 25 mol %.

When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Structural Unit (a4))

The structural unit (a4) is a structural unit containing an acid non-dissociable cyclic group. When the component (A1) includes the structural unit (a4), dry etching resistance of the resist pattern to be formed is improved. Further, the hydrophobicity of the component (A1) is further improved. Increase in the hydrophobicity contributes to improvement in terms of resolution, shape of the resist pattern and the like, particularly in an organic solvent developing process.

An "acid non-dissociable, aliphatic cyclic group" in the structural unit (a4) refers to a cyclic group which is not dissociated by the action of acid generated from the component (B) described later upon exposure, and remains in the structural unit.

As the structural unit (a4), a structural unit which contains a non-acid-dissociable aliphatic cyclic group, and is also derived from an acrylate ester is preferable. Examples of this cyclic group include the same groups as those described above in relation to the aforementioned structural unit (a1), and any of the multitude of conventional groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-7) shown below.

[Chemical Formula 28]

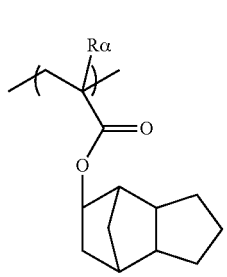
(a4-1)

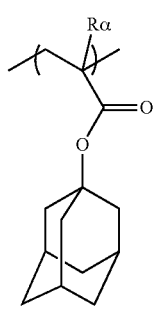
(a4-2)

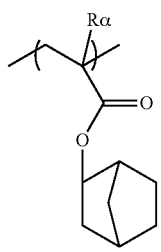
(a4-3)

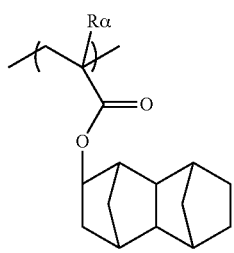
(a4-4)

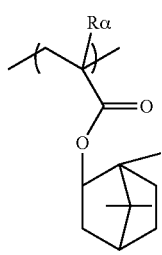
(a4-5)

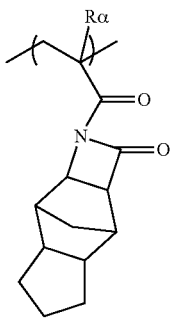

(a4-6)

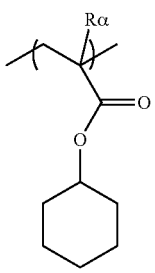

(a4-7)

In the formulae, $R^\alpha$ represents a hydrogen atom, a methyl group or a trifluoromethyl group.

As the structural unit (a4) contained in the component (A1), 1 type of structural unit may be used, or 2 or more types may be used.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

The component (A1) is preferably a copolymer having (a1) and (a2), a copolymer having (a1), (a2) and (a4) or a copolymer having (a1), (a2) and (a3). Among these, a copolymer having (a1) and (a2) or a copolymer having (a1), (a2) and (a4) is more preferable.

The component (A1) can be obtained, for example, by a conventional radical polymerization or the like of the monomers corresponding with each of the structural units, using a radical polymerization initiator such as azobisisobutyronitrile (AIBN) or dimethyl 2,2'-azobis(isobutyrate).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

In the present invention, the weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

As the component (A), one type may be used alone, or two or more types may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved.

In the present embodiment, as the component (A), one kind of compound may be used, or two or more kinds of compounds may be used in combination.

In the present embodiment, the amount of the component (A) can be appropriately adjusted depending on the thickness of the resist film to be formed, and the like.

<Acid Generator Component; Component (B)>

In the present invention, the resist composition includes an acid generator component (B) (hereafter, referred to as "component (B)") which generates acid upon exposure. The component (B) contains a compound (B0-1) represented by general formula (b0) shown below.

[Chemical Formula 29]

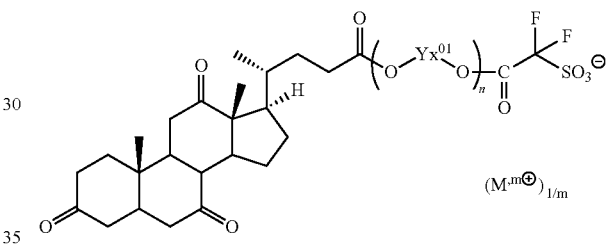

(b0)

In the formula, $Yx^{01}$ represents a divalent linking group; n represents an integer of 1 to 3; and $M'^{m+}$ represents an organic cation having a valency of m.

{Anion Moiety}

In formula (b0), $Yx^{01}$ represents a divalent linking group. The divalent linking group for $Yx^{01}$ is preferably a divalent hydrocarbon group optionally having a substituent.

The hydrocarbon group as a divalent linking group may be either an aliphatic hydrocarbon group or an aromatic hydrocarbon group.

(Aliphatic Hydrocarbon Group)

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof. More specific examples include a linear or branched aliphatic hydrocarbon group, and an aliphatic hydrocarbon group containing a ring in the structure thereof.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and a carbonyl group.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

(Aromatic Hydrocarbon Group)

The aromatic hydrocarbon group is a hydrocarbon group having an aromatic ring.

The aromatic hydrocarbon group as the divalent hydrocarbon group for Yx$^{01}$ preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

n represents an integer of 1 to 3.

Specific examples of the anion moiety of the compound (B0-1) represented by general formula (b0) are shown below.

[Chemical Formula 30]

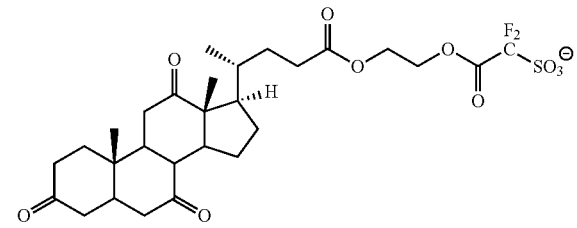

-continued

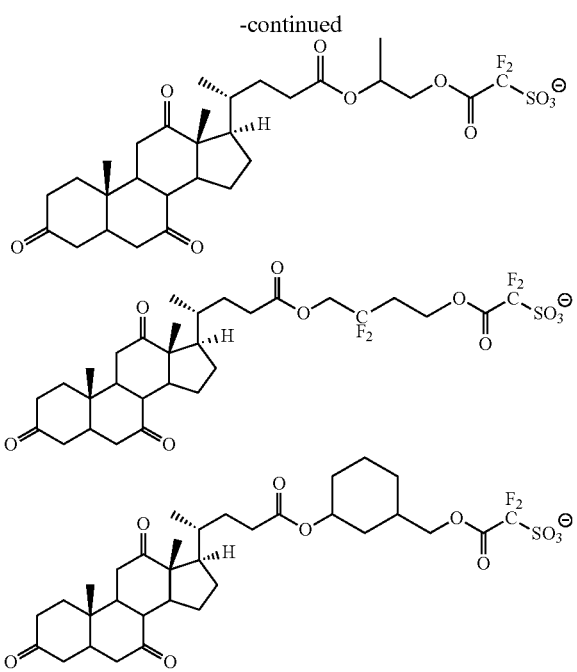

{Cation Moiety}

In formula (b0), $M'^{m+}$ represents an organic cation having a valency of m, preferably a sulfonium cation or an iodonium cation, and most preferably a cation represented by any one of formulae (ca-1) to (ca-4) shown below.

[Chemical Formula 31]

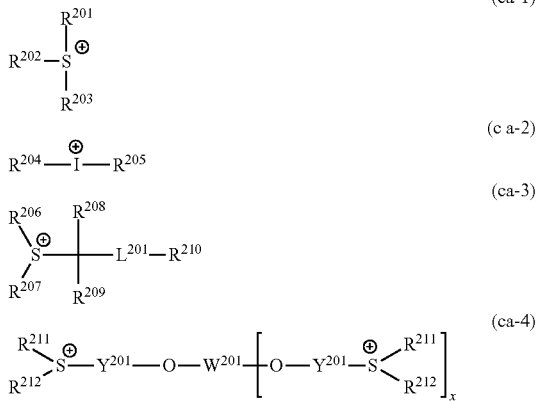

In the formulae, $R^{201}$ to $R^{207}$, $R^{211}$ and $R^{212}$ independently represents an aryl group, an alkyl group or an alkenyl group, provided that two of $R^{201}$ to $R^{203}$, $R^{206}$ and $R^{207}$, or $R^{211}$ and $R^{212}$ be mutually bonded to form a ring with the sulfur atom; $R^{208}$ and $R^{209}$ each independently represents a hydrogen atom or an alkyl group of 1 to 5 carbon atoms; $R^{210}$ represents an aryl group which may have a substituent, an alkyl group which may have a substituent, an alkenyl group which may have a substituent or an —$SO_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$ an unsubstituted aryl group of 6 to 20 carbon atoms can be mentioned, and a phenyl group or a naphthyl group is preferable.

The alkyl group for $R^{201}$ to $R^{207}$, $R^{211}$ and $R^{212}$ is preferably a chain-like or cyclic alkyl group having 1 to 30 carbon atoms.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, an arylthio group and groups represented by formulae (ca-r-1) to (ca-r-7) shown below.

The aryl group within the arylthio group as the substituent is the same as defined for $R^{101}$, and specific examples include a phenylthio group and a biphenylthio group.

[Chemical Formula 32]

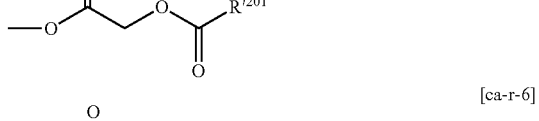

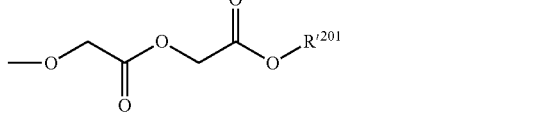

In the formulae, $R'^{201}$ each independently represents a hydrogen atom, a cyclic group which may have a substituent, a chain-like alkyl group which may have a substituent or a chain-like alkenyl group which may have a substituent.

As the cyclic group which may have a substituent, the chain-like alkyl group which may have a substituent and the chain-like alkenyl group which may have a substituent for $R'^{201}$ the same groups as those described above for $R^{101}$ can be mentioned. As the cyclic group which may have a substituent and chain-like alkyl group which may have a substituent, the same groups as those described above for the acid dissociable group represented by the aforementioned formula (a1-r-2) can be also mentioned.

When $R^{201}$ to $R^{203}$, $R^{206}$, $R^{207}$, $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group of 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ and $R^{209}$ each independently represents a hydrogen atom or an alkyl group of 1 to 5 carbon atoms, preferably a hydrogen atom or an alkyl group of 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an —SO$_2$— containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

As the —SO$_2$— containing cyclic group for $R^{210}$ which may have a substituent, the same "—SO$_2$— containing cyclic groups" as those described above for Ra$^{21}$ in the aforementioned general formula (a2-1) can be mentioned, and the group represented by the aforementioned general formula (a5-r-1) is preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{101}$ in the aforementioned formula (b-1).

The alkylene group and the alkenylene group for $Y^{201}$ is the same as defined for the aliphatic hydrocarbon group as the divalent linking group represented by Va$^1$ in the aforementioned general formula (a1-1).

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups as those described above for Ya$^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) include cations represented by formulae (ca-1-1) to (ca-1-63) shown below.

[Chemical Formula 33]

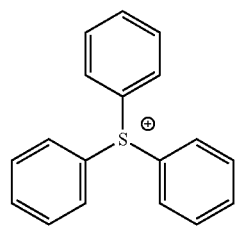

(ca-1-1)

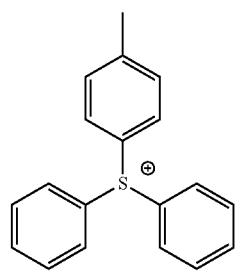

(ca-1-2)

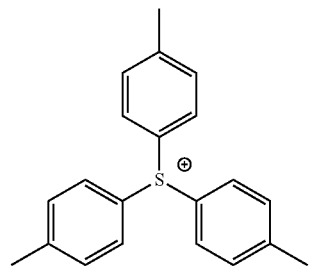

(ca-1-3)

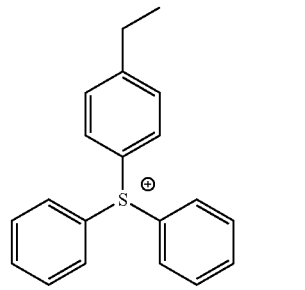

(ca-1-4)

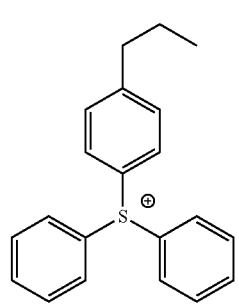

(ca-1-5)

(ca-1-6)
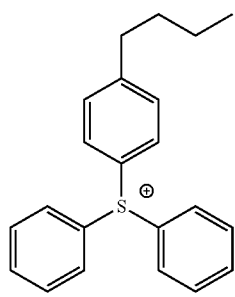
(ca-1-7)
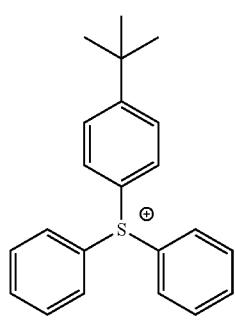
(ca-1-8)
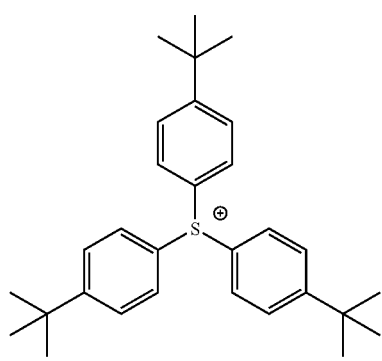
(ca-1-9)
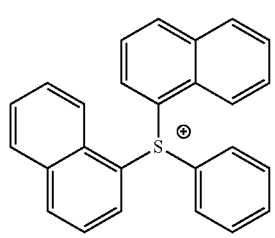
(ca-1-10)
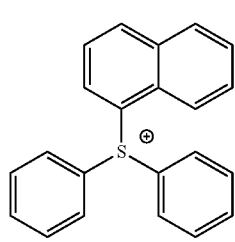
(ca-1-11)
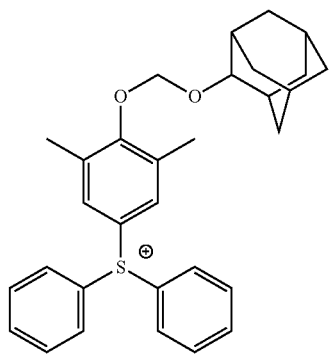
(ca-1-12)
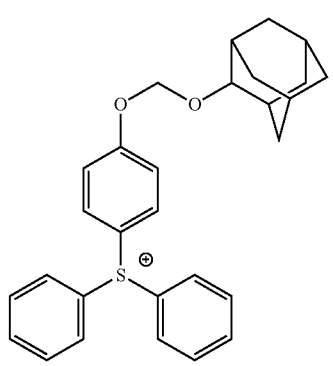
(ca-1-13)
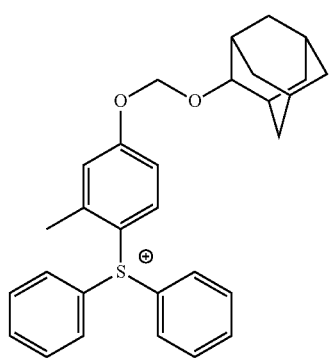
(ca-1-14)
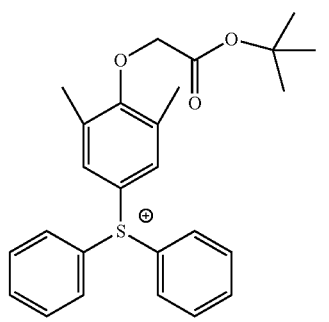

(ca-1-15)
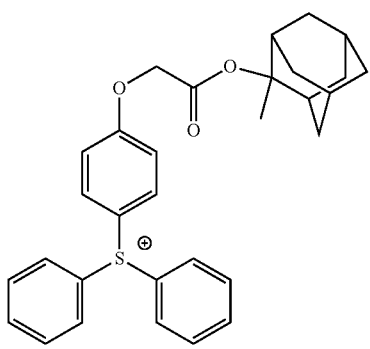
(ca-1-19)
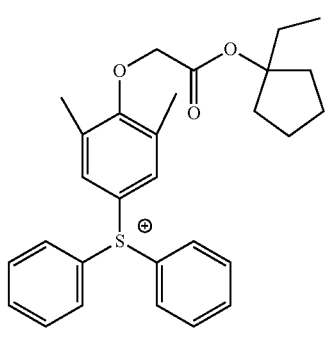
(ca-1-16)
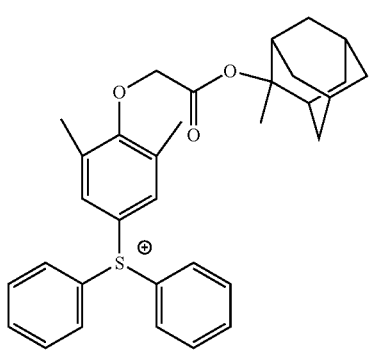
(ca-1-20)
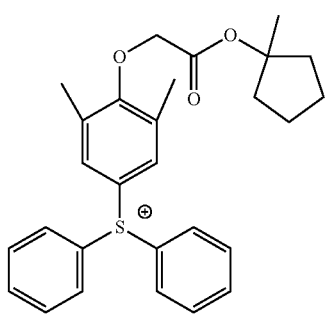
[Chemical Formula 34]
(ca-1-17)
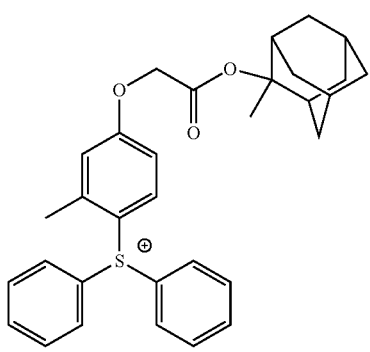
(ca-1-21)
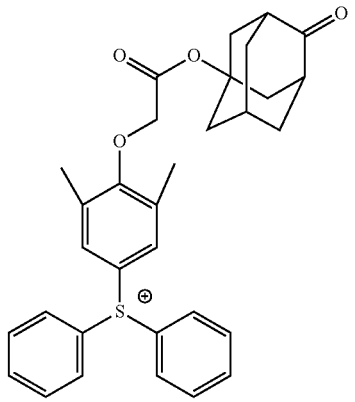
(ca-1-18)
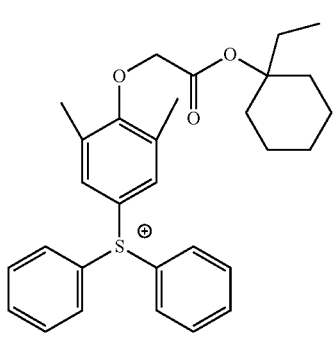
(ca-1-22)
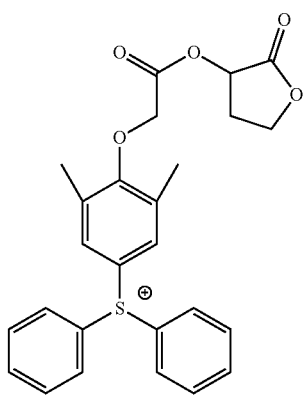

(ca-1-23)
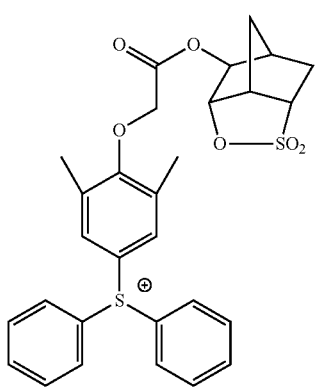
(ca-1-24)
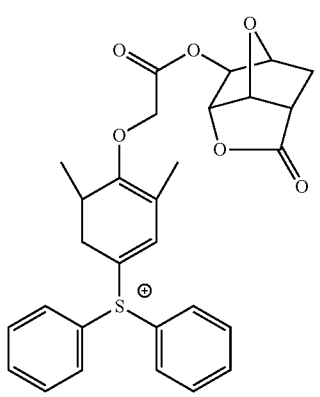
(ca-1-25)
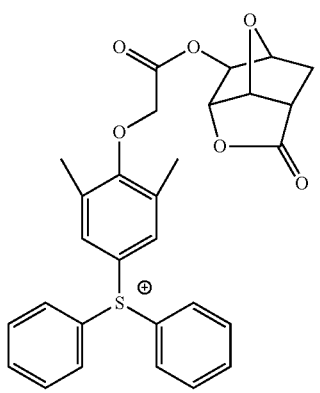
(ca-1-26)
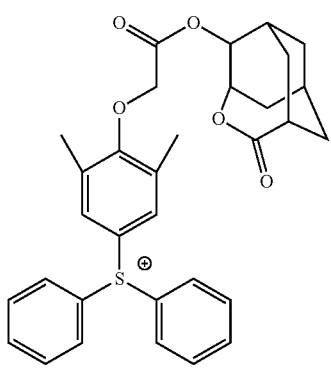
(ca-1-27)
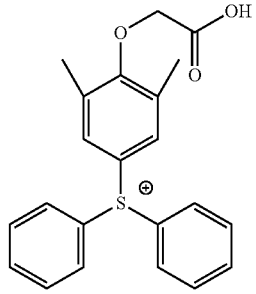
(ca-1-28)
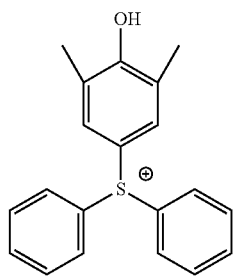
(ca-1-29)
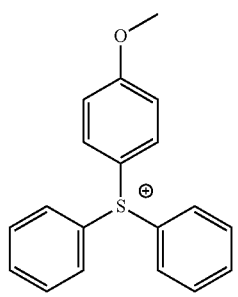
(ca-1-30)
(ca-1-31)
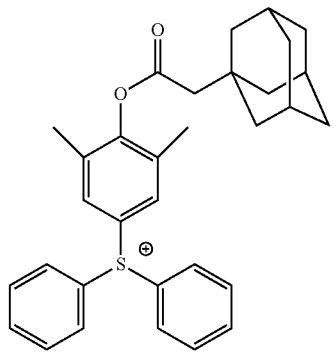

(ca-1-32)
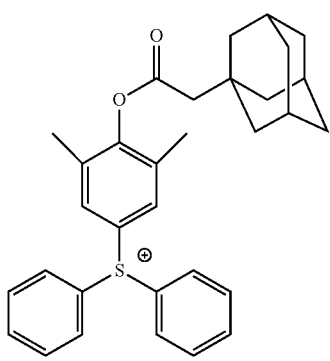
(ca-1-33)
(ca-1-36)
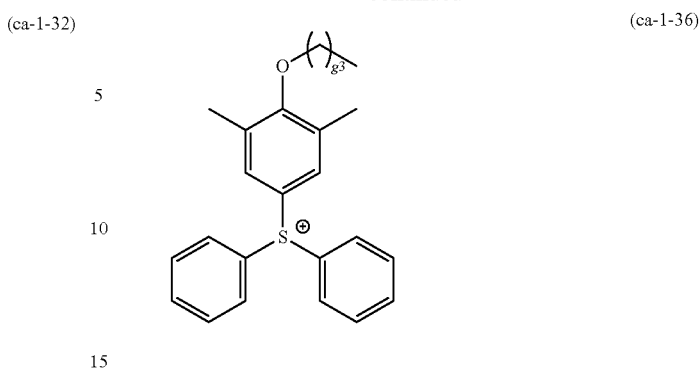
(ca-1-37)
[Chemical Formula 35]
(ca-1-34)
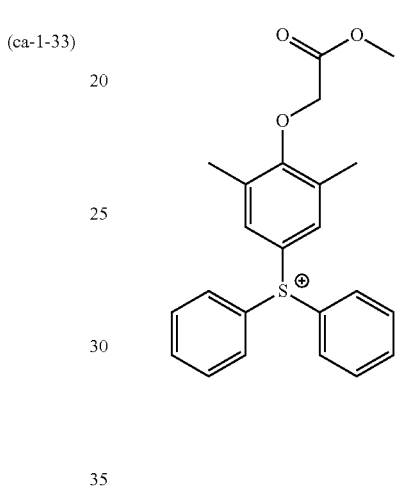
(ca-1-38)
(ca-1-35)
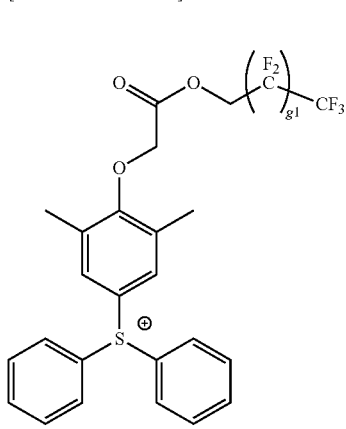
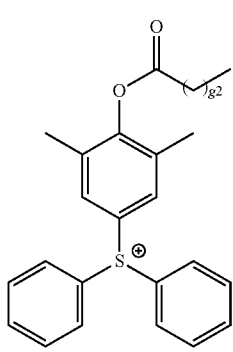
(ca-1-39)

(ca-1-40)
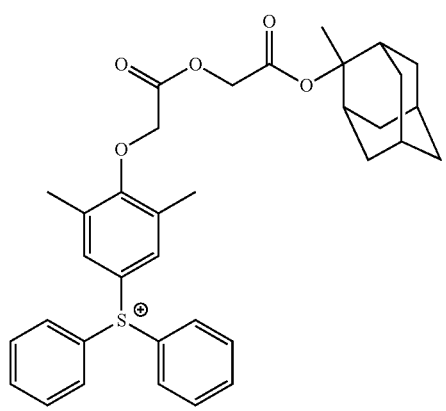
(ca-1-41)
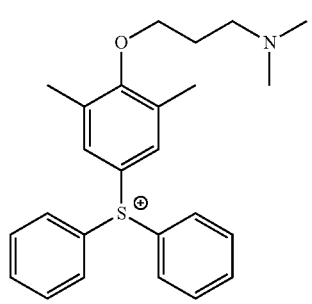
(ca-1-42)
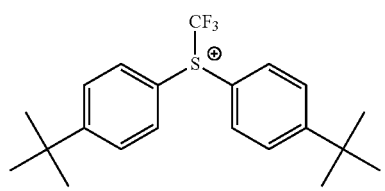
(ca-1-43)
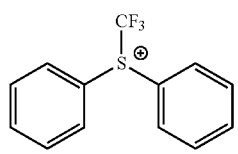
(ca-1-44)
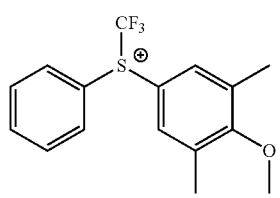
(ca-1-45)
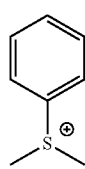
(ca-1-46)
(ca-1-47)
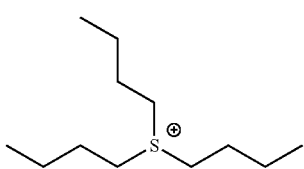
(ca-1-48)
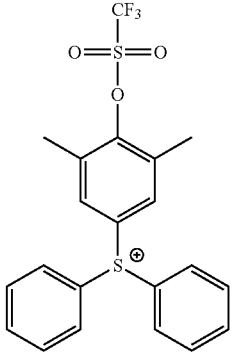
In the formulae, g1, g2 and g3 represent recurring numbers, wherein g1 is an integer of 1 to 5, g2 is an integer of 0 to 20, and g3 is an integer of 0 to 20.
[Chemical Formula 36]
(ca-1-49)
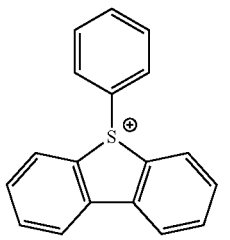
(ca-1-50)
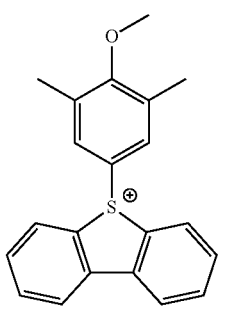
(ca-1-51)
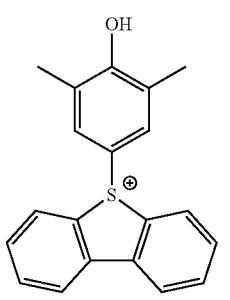

(ca-1-52)
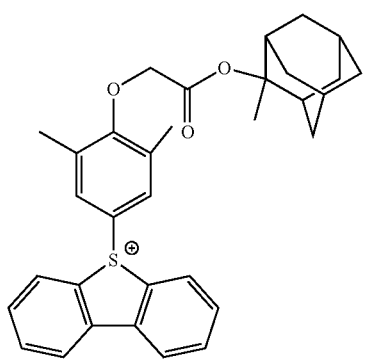
(ca-1-53)
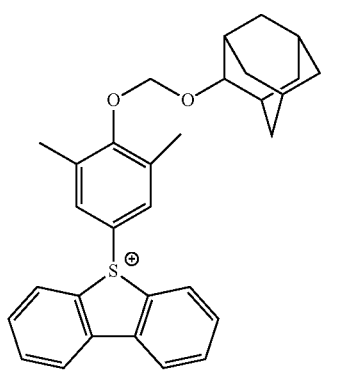
(ca-1-54)
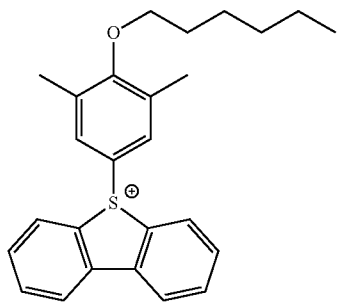
(ca-1-55)
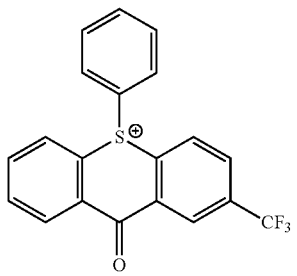
(ca-1-56)
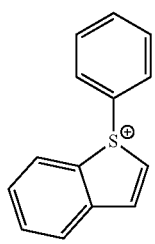
(ca-1-57)
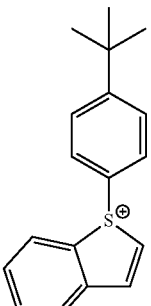
(ca-1-58)
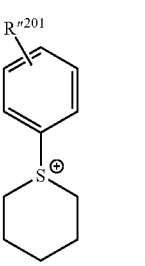
(ca-1-59)
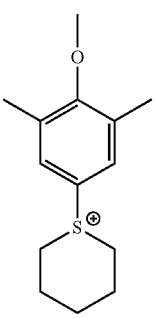
(ca-1-60)
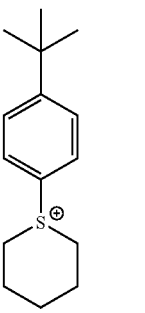
(ca-1-61)
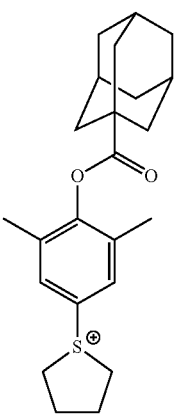

-continued

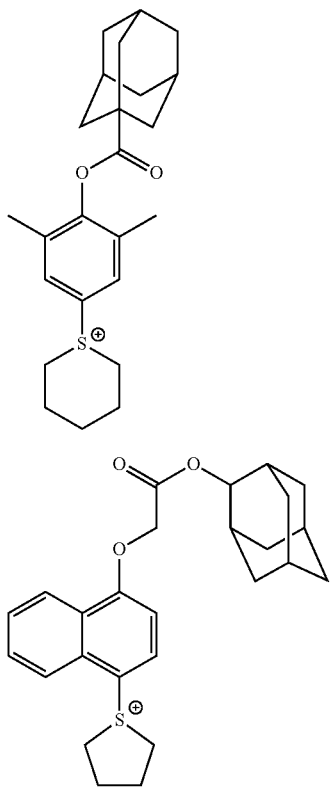

(ca-1-62)

(ca-1-63)

In the formulae, $R''^{201}$ represents a hydrogen atom or a substituent, and as the substituent, the same groups as those described above for substituting $R^{201}$ to $R^{207}$ and $R^{210}$ to $R^{212}$ can be mentioned.

Specific examples of preferable cations represented by formula (ca-3) include cations represented by formulae (ca-3-1) to (ca-3-6) shown below.

[Chemical Formula 37]

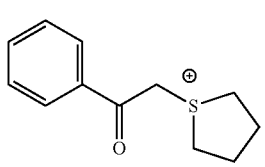

(ca-3-1)

-continued

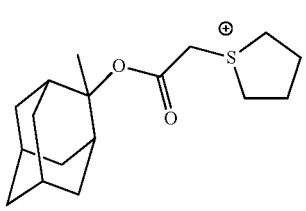

(ca-3-2)

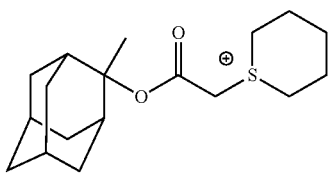

(ca-3-3)

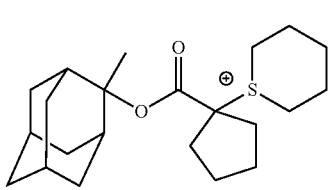

(ca-3-4)

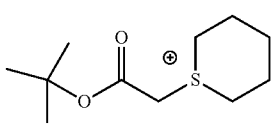

(ca-3-5)

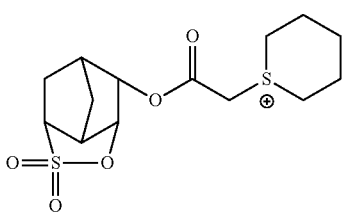

(ca-3-6)

Specific examples of preferable cations represented by formula (ca-4) include cations represented by formulae (ca-4-1) and (ca-4-2) shown below.

[Chemical Formula 38]

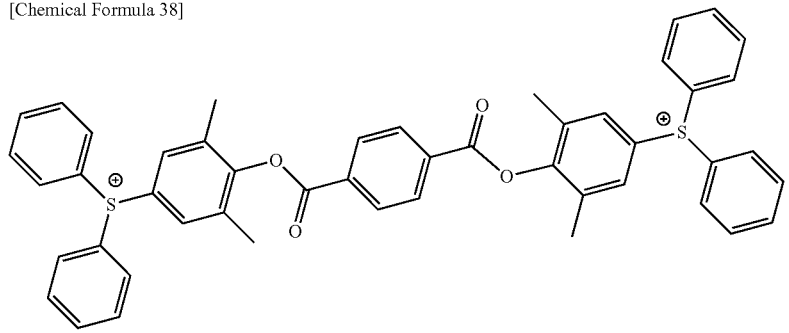

(ca-4-1)

-continued

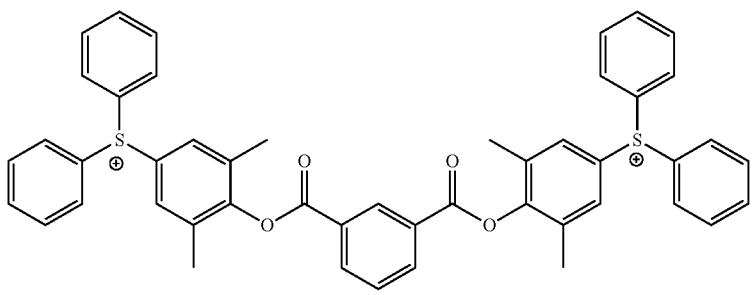
(ca-4-2)

Specific examples of the compound (B0-1) are shown below.

[Chemical Formula 39]

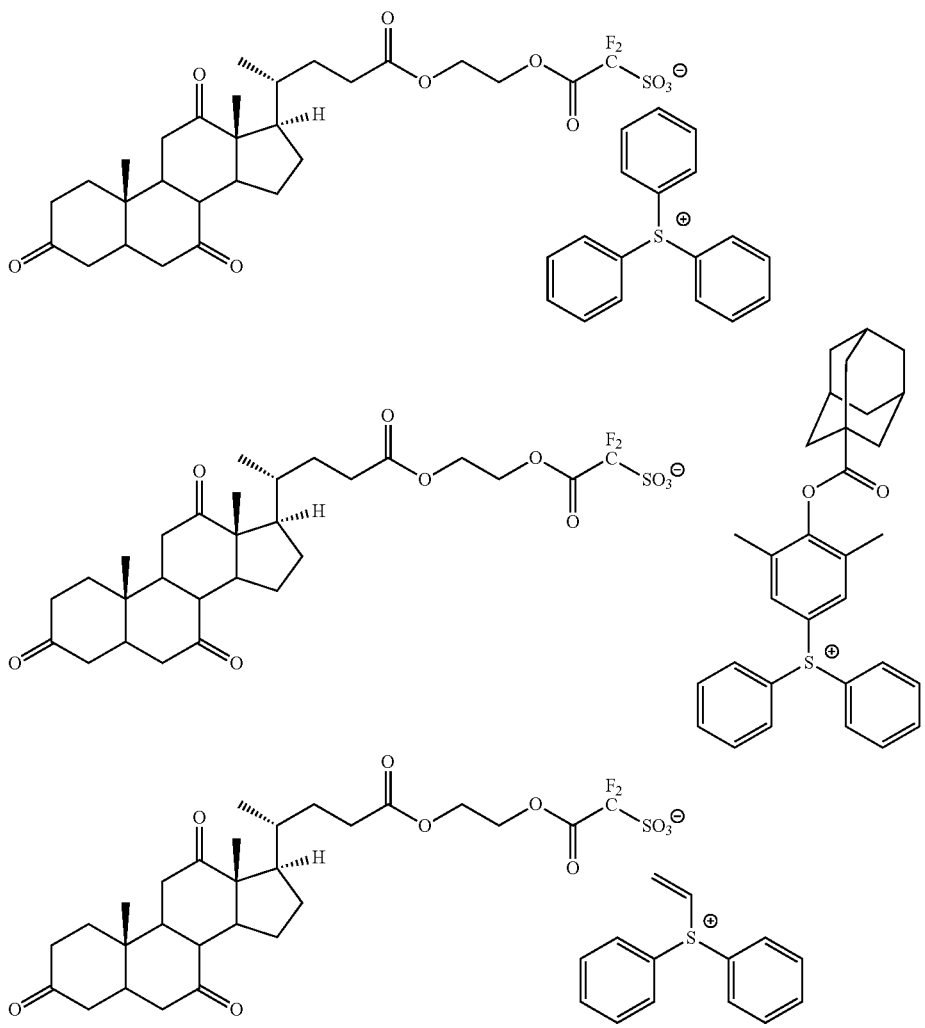

As the component (B), one type of these acid generators may be used alone, or two or more types may be used in combination.

When the resist composition of the present invention contains the component (B), the amount of the component (B) relative to 100 parts by weight of the component (A) is preferably within a range from 0.5 to 60 parts by weight, more preferably from 1 to 50 parts by weight, still more preferably from 1 to 40 parts by weight, and most preferably 1 to 20 parts by weight. When the amount of the component (B) is within the above-mentioned range, formation of a resist pattern can be satisfactorily performed. Further, by virtue of the above-mentioned range, when each of the components are dissolved in an organic solvent, a uniform solution can be obtained and the storage stability becomes satisfactory.

A resist pattern formed using the resist composition according to the present embodiment exhibits excellent lithography properties such as LWR and CDU. The reason for this is presumed as follows.

The resist composition of the present embodiment includes an acid-generator component containing the compound (B0-1). By virtue of the compound (B0-1) having a bulky steroid skeleton portion, the compound (B0-1) is capable of conducting an appropriate acid diffusion control. Further, by virtue of the linking portion of the fluorosulfonic acid terminal having a linking structure shown in the aforementioned formula (b0), it is presumed that the deprotection efficiency is improved, and as a result, lithography properties such as LWR and CDU are improved.

<Basic Compound Component; Component (D)>

The resist composition according to the present embodiment may include an acid diffusion control agent component (hereafter, frequently referred to as "component (D)"), in addition to the component (A), or in addition to the component (A) and the component (B).

The component (D) functions as an acid diffusion control agent, i.e., a quencher which traps the acid generated from the component (B) and the like upon exposure.

In the present invention, the component (D) may be a photodecomposable base (D1) (hereafter, referred to as "component (D1)") which is decomposed upon exposure and then loses the ability of controlling of acid diffusion, or a nitrogen-containing organic compound (D2) (hereafter, referred to as "component (D2)") which does not fall under the definition of component (D1).

[Component (D1)]

When a resist pattern is formed using a resist composition containing the component (D1), the contrast between exposed portions and unexposed portions is improved.

The component (D1) is not particularly limited, as long as it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions, the components (d1-1) to (d1-3) are decomposed and then lose the ability of controlling of acid diffusion (i.e., basicity), and therefore the components (d1-1) to (d1-3) cannot function as a quencher, whereas at unexposed portions, the components (d1-1) to (d1-3) functions as a quencher.

[Chemical Formula 40]

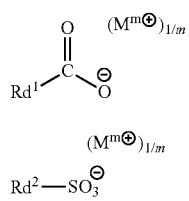

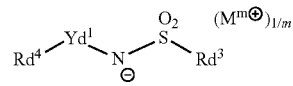

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) does not have 2 or more fluorine atoms bonded thereto; $Yd^1$ represents a single bond or a divalent linking group; and $M^{m+}$ each independently represents a cation having a valency of m.

{Component (d1-1)}
Anion Moiety

In formula (d1-1), $Rd^1$ represents a cyclic group which may have a substituent, a chain-like alkyl group which may have a substituent or a chain-like alkenyl group which may have a substituent, and is the same groups as those defined above for $R^{101}$.

Among these, as the group for $Rd^1$, an aromatic hydrocarbon group which may have a substituent, an aliphatic cyclic group which may have a substituent and a chain-like hydrocarbon group which may have a substituent are preferable. As the substituents which these groups may have, a fluorine atom or a fluorinated alkyl group is preferable.

The aromatic hydrocarbon group is preferably a phenyl group or a naphthyl group.

Examples of the aliphatic cyclic group include groups in which one or more hydrogen atoms have been removed from a polycycloalkane such as adamantane, norbornane, isobornane, tricyclodecane or tetracyclododecane.

As the chain-like hydrocarbon group, a chain-like alkyl group is preferable. The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine. Examples of the atom other than fluorine include an oxygen atom, a carbon atom, a hydrogen atom, a sulfur atom and a nitrogen atom.

As $Rd^1$, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is more preferable.

Specific examples of preferable anion moieties for the component (d1-1) are shown below.

[Chemical Formula 41]

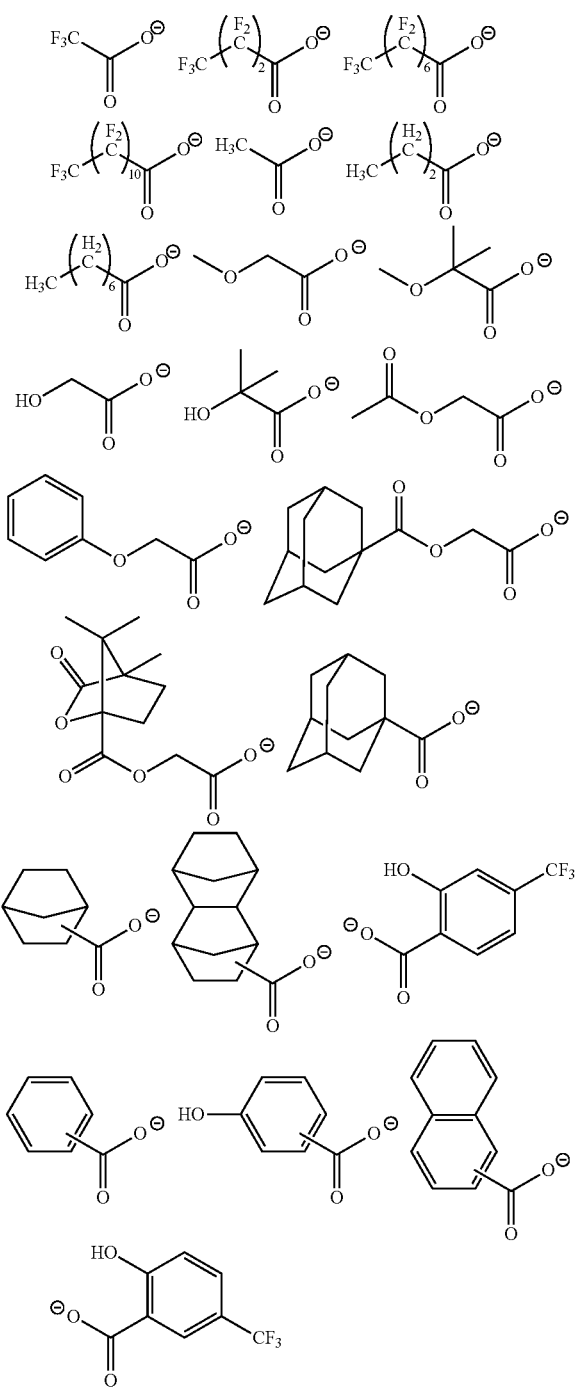

Cation Moiety

In formula (d1-1), $M^{m+}$ represents an organic cation having a valency of m.

The organic cation for $M^{m+}$ is not particularly limited, and examples thereof include the same cation moieties as those represented by the aforementioned formulas (ca-1) to (ca-4), and cation moieties represented by the aforementioned formulas (ca-1-1) to (ca-1-63) are preferable.

As the component (d1-1), one type of compound may be used, or two or more types of compounds may be used in combination.

{Component (d1-2)}
Anion Moiety

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$, provided that, the carbon atom adjacent to the sulfur atom within $Rd^2$ group does not have 2 or more fluorine atoms bonded thereto (i.e., the carbon atom adjacent to the sulfur atom within $Rd^2$ group does not substituted with a fluorine atom). As a result, the anion of the component (d1-2) becomes an appropriately weak acid anion, thereby improving the quenching ability of the component (D).

As $Rd^2$, an aliphatic cyclic group which may have a substituent is preferable, and a group in which one or more hydrogen atoms have been removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those described above for substituting the hydrocarbon group (e.g., aromatic hydrocarbon group, aliphatic hydrocarbon group) for $Rd^1$ in the formula (d1-1) can be mentioned.

Specific examples of preferable anion moieties for the component (d1-2) are shown below.

[Chemical Formula 42]

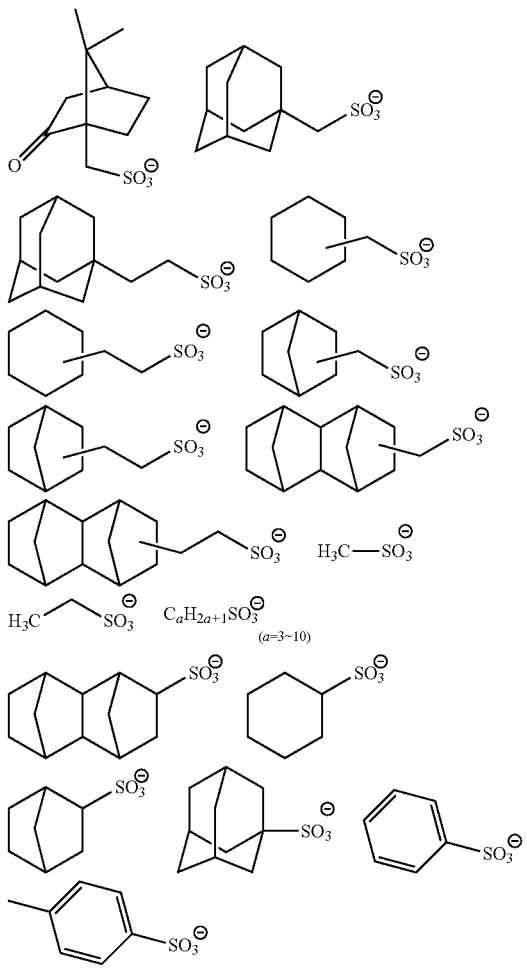

Cation Moiety

In formula (d1-2), $M^{m+}$ is an organic cation having a valency of m, and is the same as defined for $M^{m+}$ in the aforementioned formula (d1-1).

As the component (d1-2), one type of compound may be used, or two or more types of compounds may be used in combination.

{Component (d1-3)}

Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$, and a cyclic group containing a fluorine atom, a chain-like alkyl group or a chain-like alkenyl group is preferable. Among these, a fluorinated alkyl group is preferable, and more preferably the same fluorinated alkyl groups as those described above for $Rd^1$.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$.

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ can be mentioned, and a vinyl group, a propenyl group (an allyl group), a 1-methylpropenyl group and a 2-methylpropenyl group are preferable. These groups may have an alkyl group of 1 to 5 carbon atoms or a halogenated alkyl group of 1 to 5 carbon atoms as a substituent.

As the cyclic group for $Rd^4$, the same groups as those described above for $R^{101}$ can be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithography properties. Alternatively, when $Rd^4$ is an aromatic group, the resist composition exhibits an excellent photoadsorption efficiency in a lithography process using EUV or the like as the exposure source, thereby resulting in the improvement of the sensitivity and the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. As such groups, the same divalent linking groups as those described above for $Ya^{21}$ in the formula (a2-1) can be mentioned.

As $Yd^1$, a carbonyl group, an ester bond, an amide bond, an alkylene group or a combination of these is preferable. As the alkylene group, a linear or branched alkylene group is more preferable, and a methylene group or an ethylene group is still more preferable.

Specific examples of preferable anion moieties for the component (d1-3) are shown below.

[Chemical Formula 43]

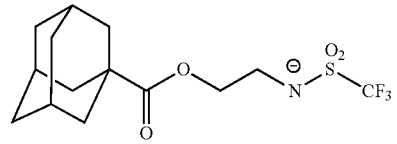

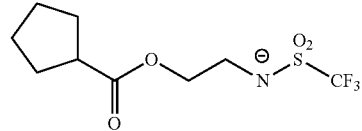

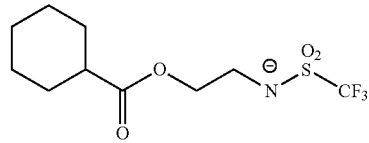

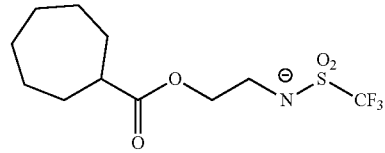

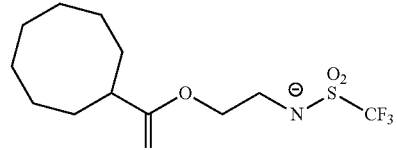

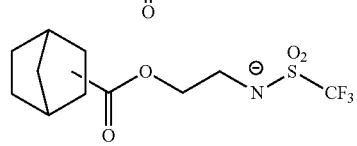

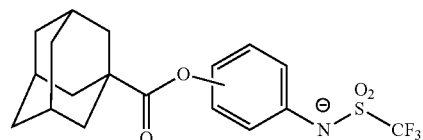

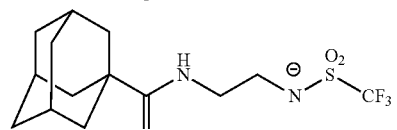

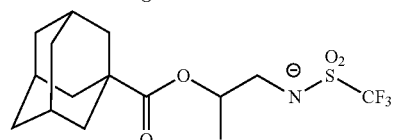

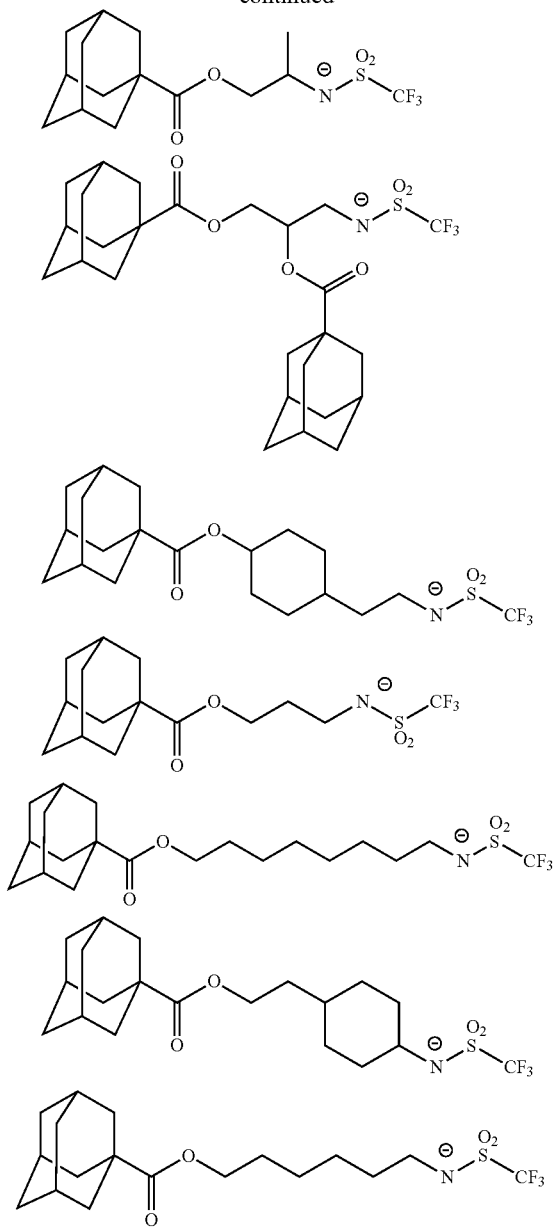

[Chemical Formula 44]

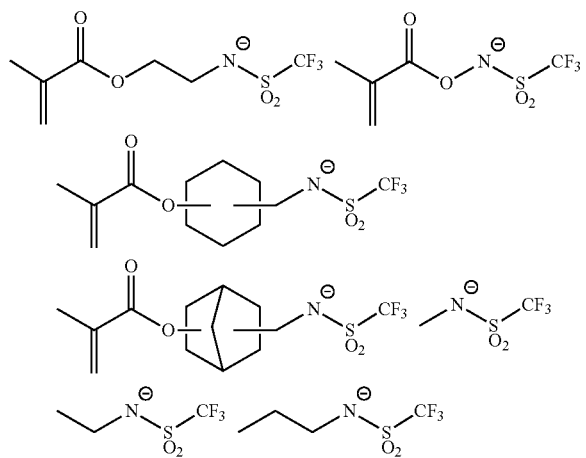

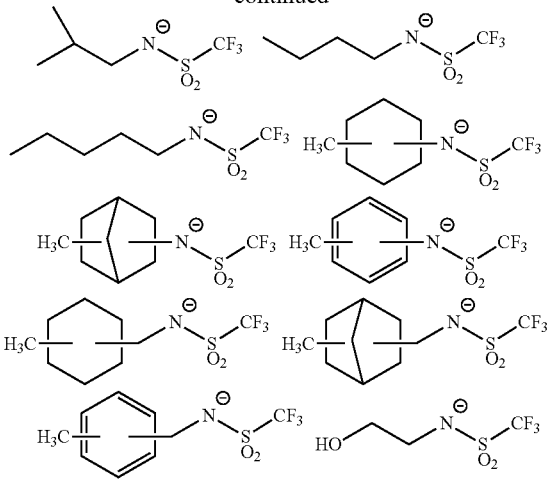

Cation Moiety

In formula (d1-3), $M^{m+}$ is an organic cation having a valency of m, and is the same as defined for $M^{m+}$ in the aforementioned formula (d1-1).

As the component (d1-3), one type of compound may be used, or two or more types of compounds may be used in combination.

As the component (D1), one type of the aforementioned components (d1-1) to (d1-3), or at least two types of the aforementioned components (d1-1) to (d1-3) can be used in combination.

The amount of the component (D1) relative to 100 parts by weight of the component (A) is preferably within a range from 0.5 to 10 parts by weight, more preferably from 0.5 to 8 parts by weight, and still more preferably from 1 to 8 parts by weight.

When the amount of the component (D1) is at least as large as the lower limit of the above-mentioned range, excellent lithography properties and excellent resist pattern shape can be obtained. On the other hand, when the amount of the component (D1) is no more than the upper limit of the above-mentioned range, sensitivity can be maintained at a satisfactory level, and through-put becomes excellent.

The production methods of the components (d1-1) and (d1-2) are not particularly limited, and the components (d1-1) and (d1-2) can be produced by conventional methods.

The amount of the component (D1) relative to 100 parts by weight of the component (A) is preferably within a range from 0.5 to 10.0 parts by weight, more preferably from 0.5 to 8.0 parts by weight, and still more preferably from 1.0 to 8.0 parts by weight. When the amount of at least as large as the lower limit of the above-mentioned range, excellent lithography properties and excellent resist pattern shape can be obtained. On the other hand, when the amount of the component (D) is no more than the upper limit of the above-mentioned range, sensitivity can be maintained at a satisfactory level, and through-put becomes excellent.

(Component (D2))

The component (D) may contain a nitrogen-containing organic compound (D2) (hereafter, referred to as component (D2)) which does not fall under the definition of component (D1).

The component (D2) is not particularly limited, as long as it functions as an acid diffusion control agent, and does not fall under the definition of the component (D1). As the component (D2), any of the conventionally known compounds may be selected for use. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl] amine and triethanolamine triacetate, and triethanolamine triacetate is preferable.

Further, as the component (D2), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D2), one type of compound may be used alone, or two or more types may be used in combination.

The component (D2) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

As the component (D), one type of compound may be used, or two or more types of compounds may be used in combination.

In the present embodiment, when the resist composition contains the component (D), the amount of the component (D) relative to 100 parts by weight of the component (A) is preferably within a range from 0.1 to 15 parts by weight, more preferably from 0.3 to 12 parts by weight, and still more preferably from 0.5 to 12 parts by weight. When the amount of the component (D) is at least as large as the lower limit of the above-mentioned range, various lithography properties (such as LWR) of the resist composition are improved. Further, a resist pattern having an excellent shape can be obtained. On the other hand, when the amount of the component (D) is no more than the upper limit of the above-mentioned range, sensitivity can be maintained at a satisfactory level, and through-put becomes excellent.

<Optional Components>

[Component (E)]

In the present invention, in the resist composition, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one type may be used alone, or two or more types may be used in combination.

The component (E) is typically used in an amount within a range from 0.01 to 5.0 parts by weight, relative to 100 parts by weight of the component (A).

[Component (F)]

In the present invention, the resist composition of the present invention may contain a fluorine additive (hereafter, referred to as "component (F)") for imparting water repellency to the resist film.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of a structural unit (f1) represented by formula (f1-1) shown below and the aforementioned structural unit (a1); and a copolymer of a structural unit (f1) represented by formula (f1-1) shown below, a structural unit derived from acrylic acid or methacrylic acid and the aforementioned structural unit (a1) are preferable. As the structural unit (a1) to be copolymerized with a structural unit (f1) represented by formula (f1-1) shown below, a structural unit derived from 1-ethyl-1-cyclooctyl (meth)acrylate or a structural unit represented by the aforementioned formula (a1-2-01) is preferable.

[Chemical Formula 45]

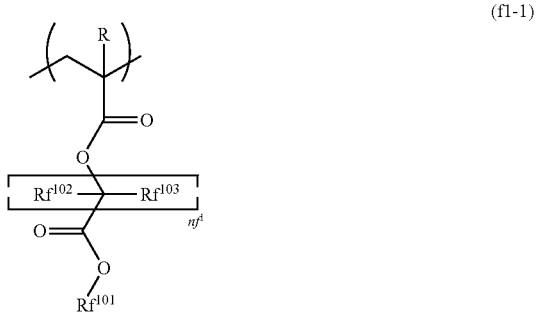

(f1-1)

In the formula, R is the same as defined above; $Rf^{102}$ and $Rf^{103}$ each independently represents a hydrogen atom, a halogen atom, an alkyl group of 1 to 5 carbon atoms, or a halogenated alkyl group of 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly desirable. Examples of the alkyl group of 1 to 5 carbon atoms for $Rf^{102}$ and $Rf^{103}$ include the same alkyl group of 1 to 5 carbon atoms as those described above for R, and a methyl group or an ethyl group is preferable. Specific examples of the halogenated alkyl group of 1 to 5 carbon atoms represented by $Rf^{102}$ or $Rf^{103}$ include groups in which part or all of the hydrogen atoms of the aforementioned alkyl groups of 1 to 5 carbon atoms have been substituted with halogen atoms. Examples of the halogen atom include a fluorine atom, a chlorine atom, a bromine atom and an iodine atom, and a fluorine atom is particularly desirable. Among these, as $Rf^{102}$ and $Rf^{103}$, a hydrogen atom, a fluorine atom or an alkyl group of 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group of 1 to 5 carbon atoms is preferable, and a methyl group, —$CH_2$—$CF_3$, —$CH_2$—$CF_2$—$CF_3$, —$CH(CF_3)_2$, —$CH_2$—$CH_2$—$CF_3$, and —$CH_2$—$CH_2$—$CF_2$—$CF_2$—$CF_2$—$CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one type may be used alone, or two or more types may be used in combination.

The component (F) is generally used in an amount within a range from 0.5 to 10 parts by weight, relative to 100 parts by weight of the component (A).

In the present invention, if desired, other miscible additives can also be added to the resist composition. Examples of such miscible additives include additive resins for improving the performance of the resist film, dissolution inhibitors, plasticizers, stabilizers, colorants, halation prevention agents, and dyes.

[Component (S)]

In the present invention, the resist composition can be prepared by dissolving the materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone (MEK), cyclohexanone, methyl-n-pentyl ketone (2-heptanone), methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, PGMEA, PGME, γ-butyrolactone and EL are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate In general, the organic solvent is used in an amount such that the solid content of the resist composition becomes within the range from 1 to 20% by weight, and preferably from 2 to 15% by weight.

<<Method of Forming a Resist Pattern>>

In the present embodiment, a resist pattern may be formed by forming a resist film on a substrate using the aforementioned resist composition; exposing the resist film; and developing the resist film to form a resist pattern.

The method for forming a resist pattern may be performed, for example, as follows.

Firstly, the aforementioned resist composition is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment.

The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing. In this manner, a resist pattern can be obtained.

In the present embodiment, the developing treatment may be either an alkali developing process or a solvent developing process.

(Substrate)

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the component (A) (prior to exposure). Specific examples of the organic solvent include polar solvents such as ketone solvents, ester solvents, alcohol solvents, amide solvents and ether solvents, and hydrocarbon solvents.

If desired, the organic developing solution may have a conventional additive blended. Examples of the additive include surfactants. The surfactant is not particularly limited, and for example, an ionic or non-ionic fluorine and/or silicon surfactant can be used.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

<<Acid Generator>>

A third aspect of the present invention is an acid generator containing a compound (B0-1) represented by general formula (b0) shown below.

[Chemical Formula 46]

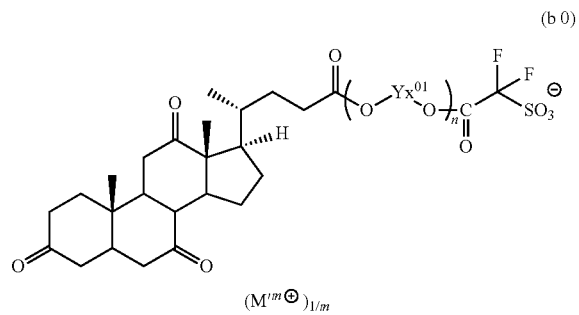

(b0)

In the formula, $Yx^{01}$ represents a divalent linking group; n represents an integer of 1 to 3; and $M'^{m+}$ represents an organic cation having a valency of m.

In the acid generator of the present invention, the compound (B0-1) represented by general formula (b0) is the same as defined for the compound (B0-1) represented by general formula (b0) described above in relation to the resist composition according to the first aspect.

<<Compound>>

A fourth aspect of the present invention is a compound represented by general formula (b0) shown below.

[Chemical Formula 47]

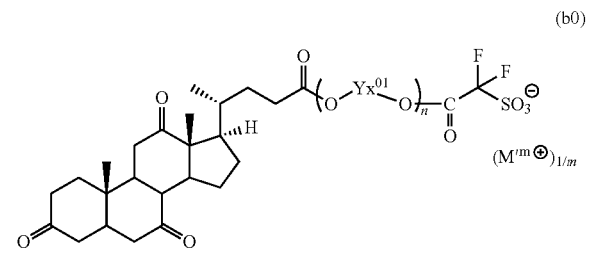

(b0)

In the formula, $Yx^{01}$ represents a divalent linking group; n represents an integer of 1 to 3; and $M'^{m+}$ represents an organic cation having a valency of m.

In the compound of the present invention, the compound represented by general formula (b0) is the same as defined for the compound (B0-1) represented by general formula (b0) described above in relation to the resist composition according to the first aspect.

<<Production Method of Compound>>

The production method of the compound of the present invention will be described. The method for producing the compound (B0-1) is not particularly limited, and the compound (B0-1) can be produced by a conventional method.

For example, the compound may be produced by a method including: a first step in which a compound represented by formula (m1) shown below is synthesized from dehydrocholic acid; a second step in which the compound represented by formula (m1) shown below is reacted with a compound represented by formula (m2) shown below to synthesize a compound represented by formula (m3) shown below; and a third step in which the obtained compound (m3) is subjected to a salt exchange to obtain a compound (B0-1).

[Chemical Formula 48]

First step

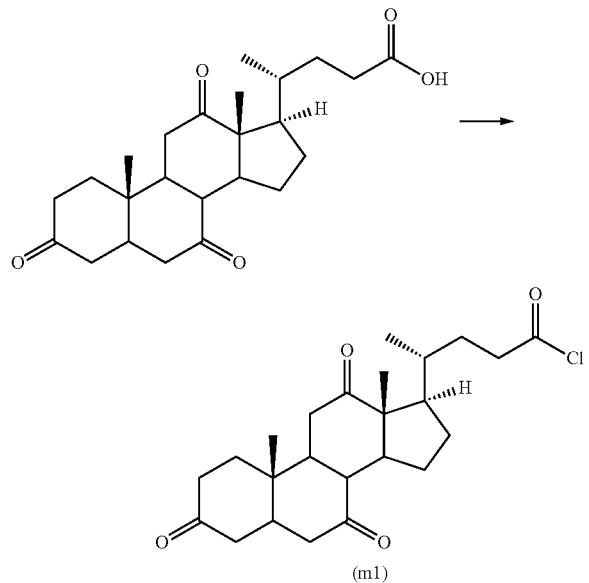

[Chemical Formula 49]

Second step

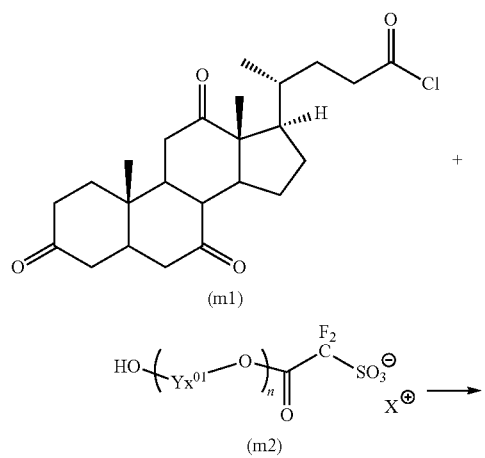

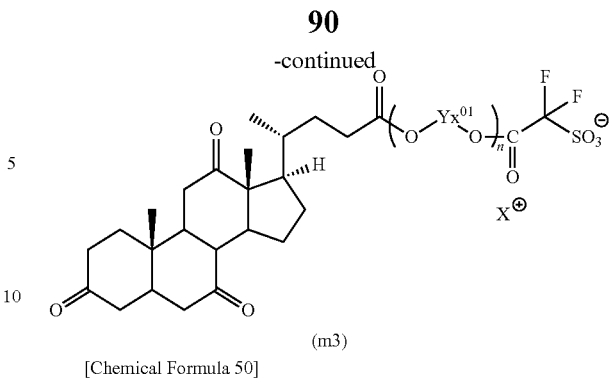

(m3)

[Chemical Formula 50]

Third step

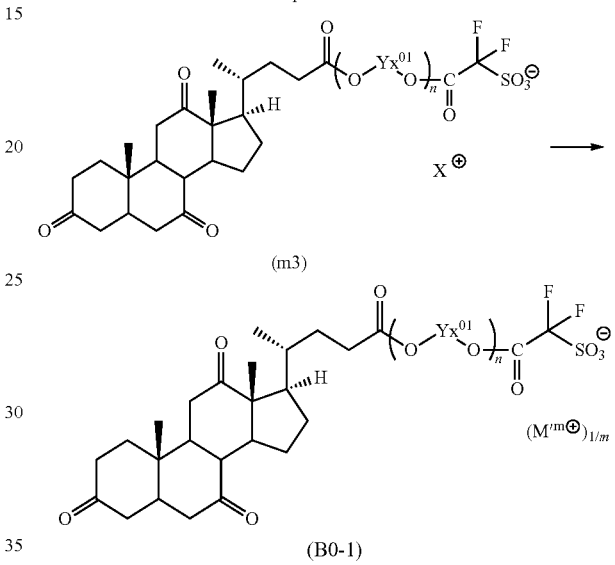

(B0-1)

In formulae (m2) and (m3), $Yx^{01}$ and n are the same as defined above. $X^+$ represents a metal cation or a nitrogen atom-containing cation.

As the compounds represented by formulae (m2) and (m3), commercially available compounds may be used, or the compounds may be synthesized by a conventional method.

The solvent used in the first and second steps may be any solvent which can dissolve dehydrocholic acid and the compounds (m1) and (m2) and which cannot react with these compounds, and for examples thereof include dichloromethane, dichloroethane, chloroform, tetrahydrofuran, N, N-dimethylformamide, acetonitrile and propionitrile.

In the third step, by salt exchanging with a desired cation, a compound (B0-1) can be derived. As the cation, a cation represented by any of the aforementioned general formulae (ca-1) to (ca-4) is most preferable.

After the reaction, the compound within the reaction mixture may be separated and purified. The separation and purification can be conducted by a conventional method. For example, any one of concentration, solvent extraction, distillation, crystallization, re-crystallization and chromatography can be used alone, or two or more of these methods may be used in combination.

The structure of the compound obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

EXAMPLES

The present invention will be described more specifically with reference to the following examples, although the scope of the present invention is by no way limited by these examples.

Compound Synthesis Example

Synthesis Example 1

To a mixed solution containing dehydrocholic acid (15.0 g) and dichloromethane (135 g) was dropwise added oxalyl chloride (6.15 g) and dimethylformamide (0.03 g), followed by stirring at room temperature for 3 hours. The obtained reaction liquid was concentrated, so as to obtain a compound represented by formula (a) (15.6 g).

The identification of the compound represented by formula (a) obtained by the above synthesis is shown below.

$^1$H NMR (DMSO-d$^6$) δ(ppm)=3.02-2.80 (m, 5H), 2.39-1.80 (m, 14H), 1.66-1.53 (m, 1H), 1.52-1.21 (m, 7H), 1.07 (S, 3H), 0.86 (d, 3H).

[Chemical Formula 51]

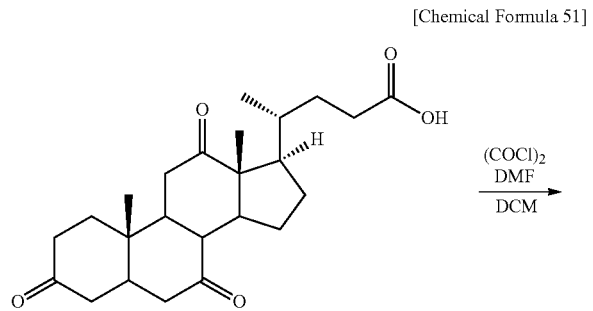

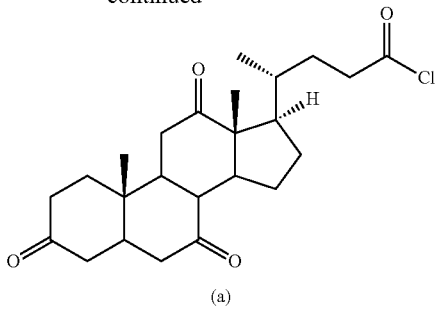

(a)

Synthesis Example 2

The compound represented by formula (a) (11.5 g), acetonitrile (105 g), a salt represented by formula (b) (9.92 g) and triethylamine (2.63 g) were mixed together, followed by stirring at room temperature for 24 hours. The obtained reaction liquid was filtered, followed by concentration. The obtained residue was dissolved in tetrahydrofuran (hereafter, referred to as "THF") (100 g), and t-butylmethylether (50.0 g) was dropwise added, so as to precipitate a white solid. Thereafter, the solvent was removed by decantation, so as to recover the white solid. The white solid was dissolved in THF (100 g), and t-butylmethylether (50.0 g) was dropwise added, so as to precipitate a white solid. The same procedure was conducted 4 times to obtain a white solid. Then, to the white solid was added dichloromethane (95.0 g) and ion exchange water (50.0 g), and stirred at room temperature for 30 minutes, followed by liquid separation to collect the organic phase. To the collected organic phase was added ion exchange water (50.0 g) and stirred at room temperature for 30 minutes, followed by liquid separation to collect the organic phase. This water washing operation was conducted twice. The obtained organic phase was concentrated, so as to obtain a salt represented by formula (c) (3.40 g).

The identification of the compound represented by formula (c) obtained by the above synthesis is shown below.

$^1$H NMR (DMSO-d$^6$) δ(ppm)=8.82 (s, 1H), 4.50-4.40 (m, 2H), 4.30-4.20 (m, 2H), 3.15-2.95 (m, 8H), 2.84 (t, 1H), 2.55-1.64 (m, 16H), 1.55-1.45 (m, 1H), 1.33-1.05 (m, 16H), 1.01 (s, 3H), 0.75 (d, 3H).

$^{19}$F NMR (DMSO-d$^6$) δ(ppm)=−106.8 (t, 2F).

[Chemical Formula 52]

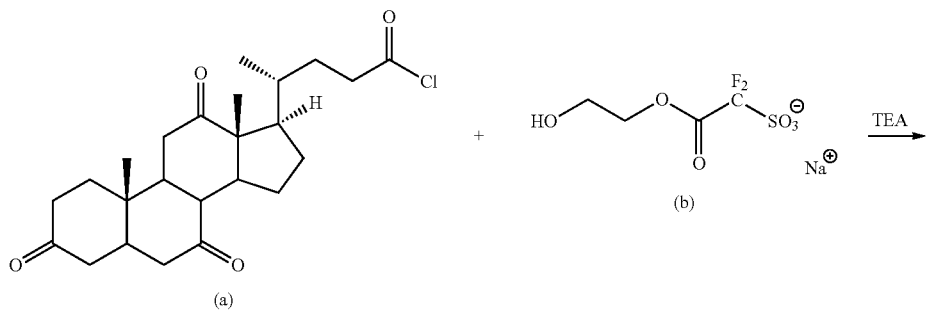

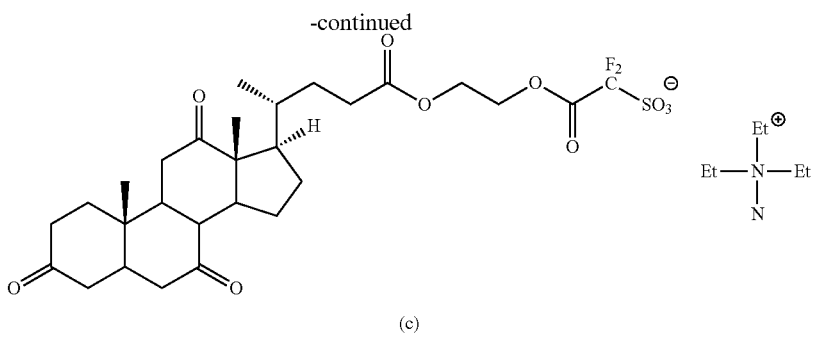

(c)

Synthesis Example 3

The salt represented by formula (c) (0.5 g), a salt represented by formula (d) (0.24 g), dichloromethane (4.5 g) and ion exchange water (5.0 g) were mixed together, and stirred at room temperature for 30 minutes, followed by liquid separation to collect the organic phase. To the collected organic phase was added ion exchange water (5.0 g) and stirred at room temperature for 30 minutes, followed by liquid separation to collect the organic phase. This water washing operation was conducted 3 times. The obtained organic phase was concentrated, so as to obtain a salt represented by formula (e) (0.46 g).

The identification of the compound represented by formula (e) obtained by the above synthesis is shown below.

$^1$H NMR (DMSO-d$^6$) δ(ppm)=7.89-7.75 (m, 15H), 4.45-4.40 (m, 2H), 4.30-4.20 (m, 2H), 3.07-2.90 (m, 2H), 2.82 (t, 1H), 2.50-1.59 (m, 16H), 1.52-1.44 (m, 1H), 1.40-1.15 (m, 7H), 1.01 (s, 3H), 0.76 (d, 3H).

$^{19}$F NMR (DMSO-d$^6$) δ(ppm)=−106.7 (s, 2F).

[Chemical Formula 53]

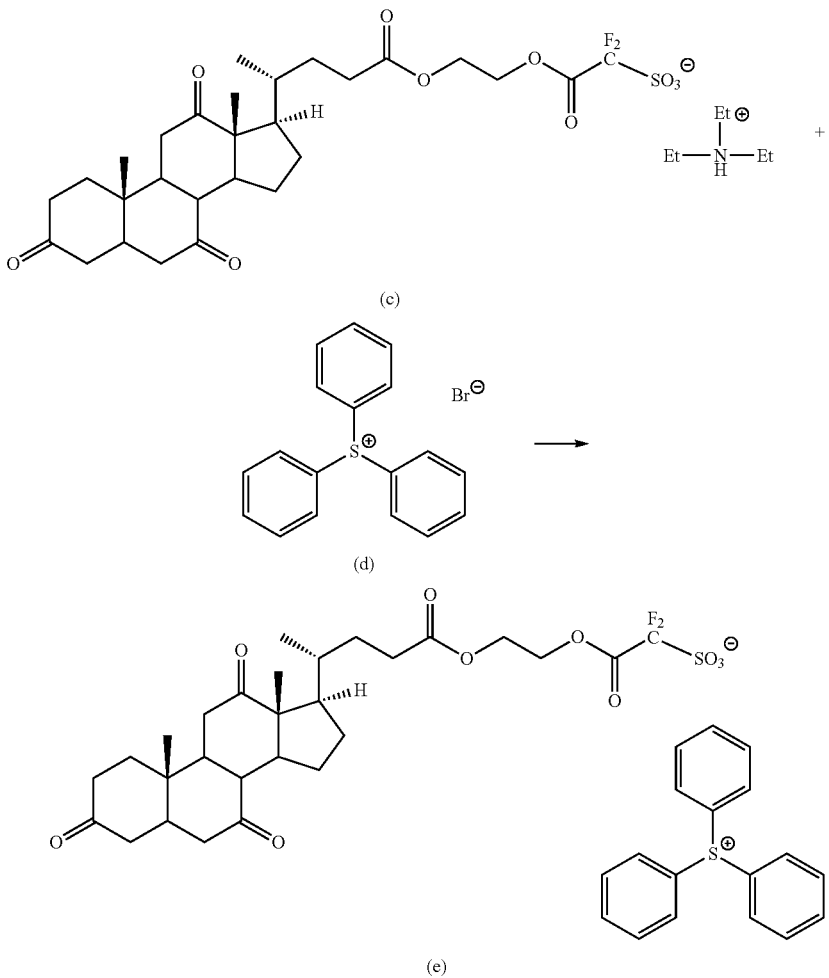

Synthesis Example 4

The same procedure as in Synthesis Example 3 was conducted, except that a compound represented by formula (f) was used instead of the salt represented by formula (d), so as to obtain 0.57 g a compound represented by formula (g).

The identification of the compound represented by formula (g) obtained by the above synthesis is shown below.

$^1$H NMR (DMSO-d$^6$) δ(ppm)=7.87-7.76 (m, 10H), 7.69 (s, 2H), 4.45-4.40 (m, 2H), 4.30-4.20 (m, 2H), 3.07-2.90 (m, 2H), 2.82 (t, 1H), 2.50-1.59 (m, 37H), 1.52-1.44 (m, 1H), 1.40-1.15 (m, 7H), 1.01 (s, 3H), 0.76 (d, 3H).

$^{19}$F NMR (DMSO-d$^6$) δ(ppm)=−106.7 (s, 2F).

[Chemical Formula 54]

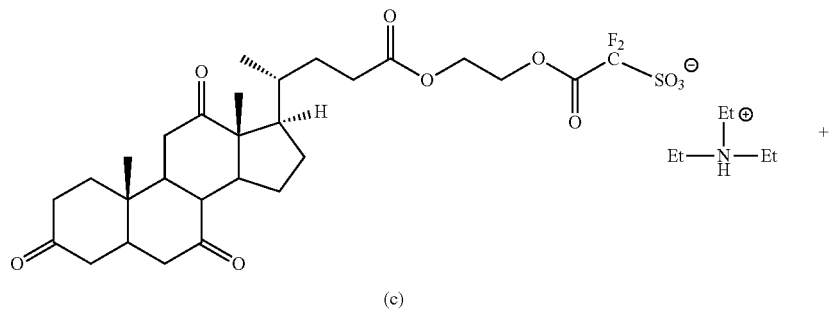

(c)

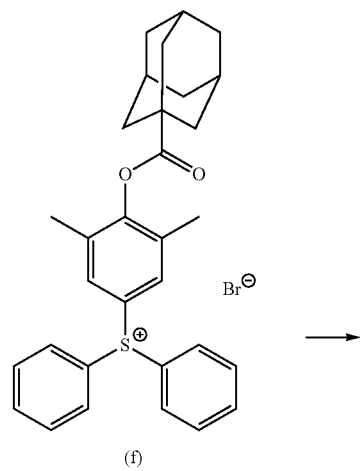

(f)

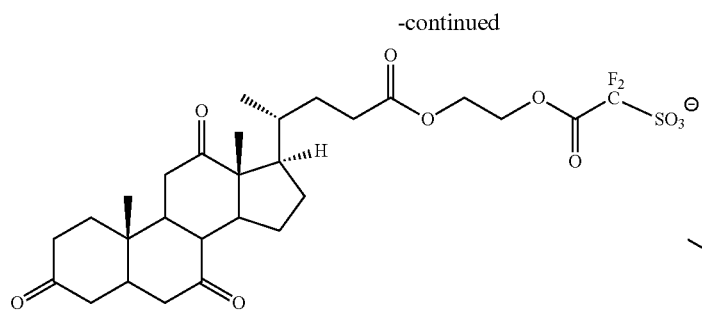
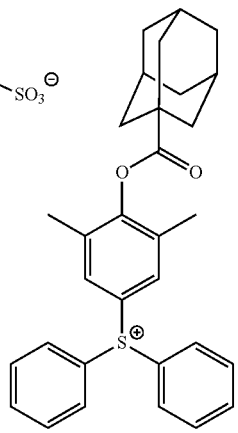

(g)

Synthesis Example 5

The same procedure as in Synthesis Example 3 was conducted, except that a compound represented by formula (h) was used instead of the salt represented by formula (d), so as to obtain 0.19 g a compound represented by formula (i).

The identification of the compound represented by formula (i) obtained by the above synthesis is shown below.

$^1$H NMR (DMSO-d$^6$) δ(ppm)=8.00-7.70 (m, 10H), 7.62 (dd, 1H), 6.82 (dd, 1H), 6.52 (dd, 1H), 4.45-4.40 (m, 2H), 4.30-4.20 (m, 2H), 3.07-2.90 (m, 2H), 2.82 (t, 1H), 2.50-1.59 (m, 16H), 1.52-1.44 (m, 1H), 1.40-1.15 (m, 7H), 1.01 (s, 3H), 0.76 (d, 3H).

$^{19}$F NMR (DMSO-d$^6$) δ(ppm)=−106.8 (s, 2F).

[Chemical Formula 55]

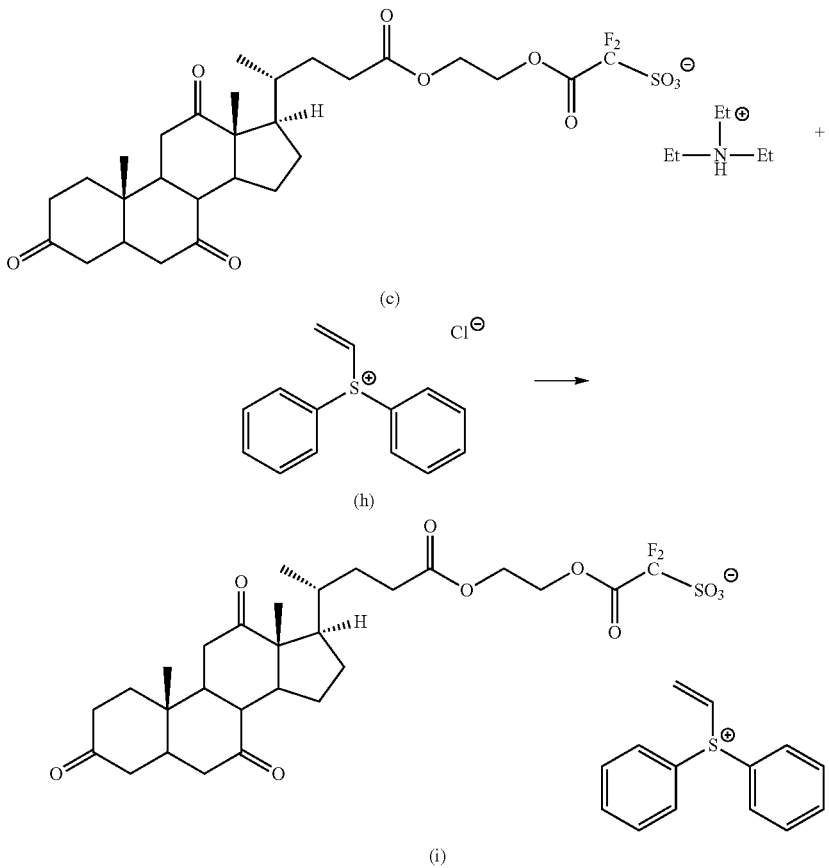

Production of Resist Composition 1: Examples 1 to 4, Comparative Examples 1 to 3

Each component (A) and each component (B) shown in Table 1, 3.25 parts by weight of compound (D)-1 shown below, 4 parts by weight of polymeric compound (F)-1 shown below, 0.2 parts by weight of salicylic acid and 4,000 parts by weight of a solvent (a mixed solvent of PGMEA/PGME/cyclohexanone (weight ratio: 45/30/25)) were mixed together, so as to produce the resist compositions of Examples 1 to 4 and Comparative Examples 1 to 3.

TABLE 1

|  | Component (A) | Component (B) |
| --- | --- | --- |
| Example 1 | (A)-1 [100] | (B)-1 [3.4] |
| Example 2 | (A)-1 [100] | (B)-2 [4.2] |
| Example 3 | (A)-1 [100] | (B)-3 [3.2] |
| Example 4 | (A)-2 [100] | (B)-1 [6.8] |
| Comparative Example 1 | (A)-1 [100] | (B)-4 [3.2] |
| Comparative Example 2 | (A)-2 [100] | (B)-4 [6.4] |
| Comparative Example 3 | (A)-2 [100] | (B)-5 [5.0] |

In Table 1, the values in brackets [ ] indicate the amount (in terms of parts by weight) of the component added.

In Table 1, (A)-1 and (A)-2 indicate polymeric compounds (A)-1 and (A)-2 shown below, respectively.

In Table 1, (B)-1 to (B)-5 indicate compounds (B)-1 to (B)-5 shown below, respectively.

[Chemical Formula 56]

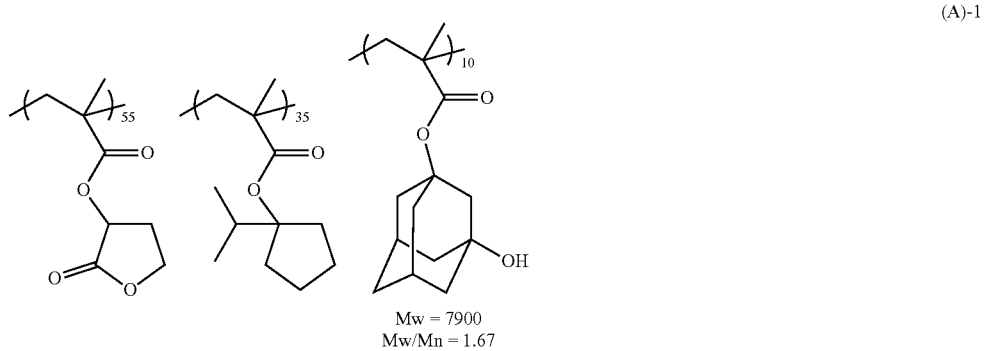

(A)-1

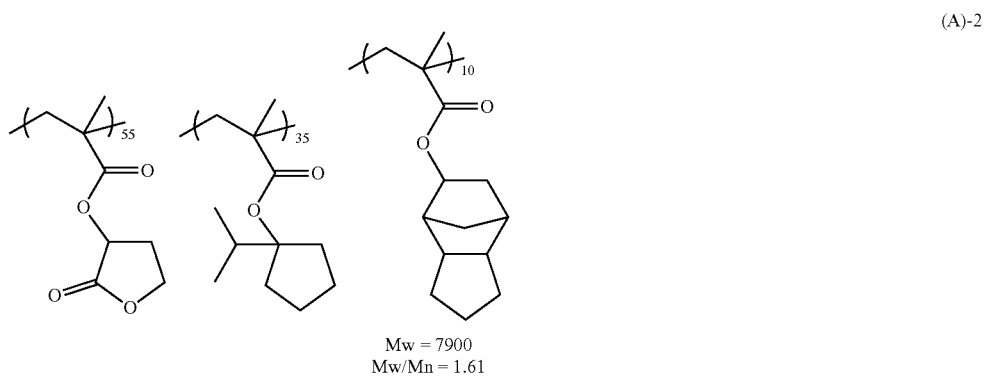

(A)-2

[Chemical Formula 57]

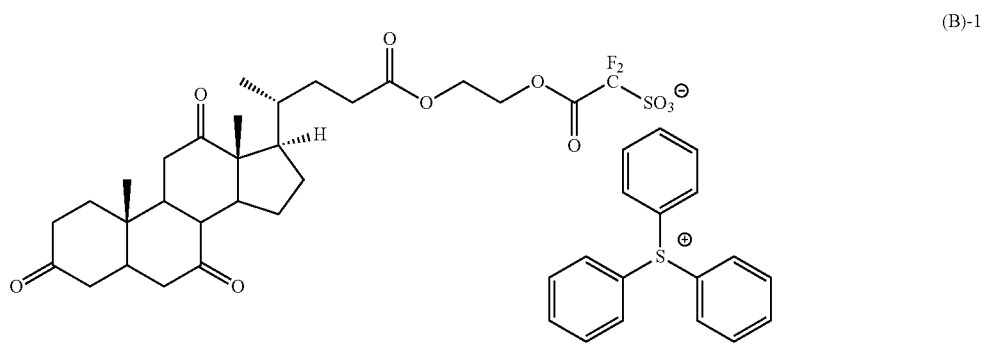

(B)-1

-continued
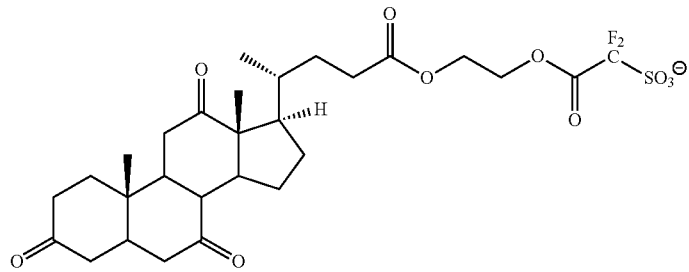
[Chemical Formula 58]
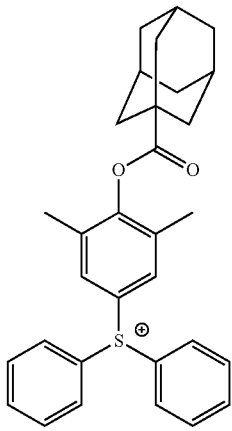
(B)-2
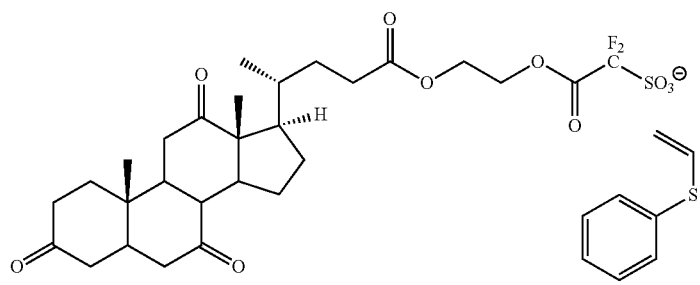
[Chemical Formula 59]
(B)-3
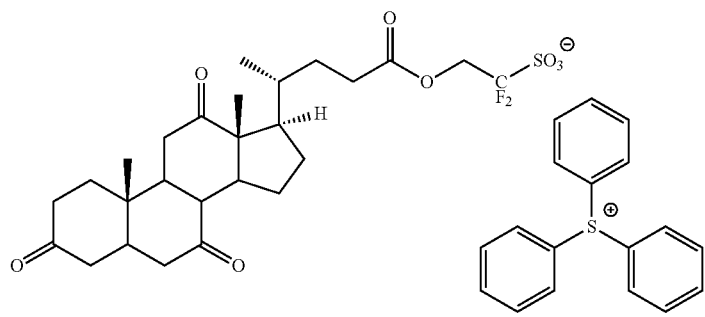
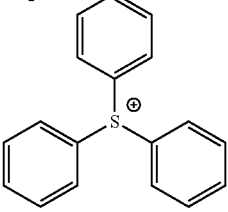
(B)-4
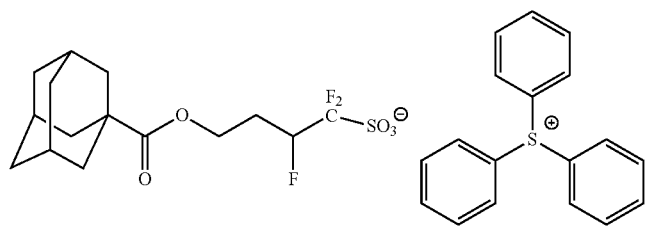
[Chemical Formula 60]
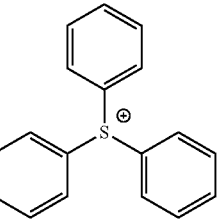
(B)-5
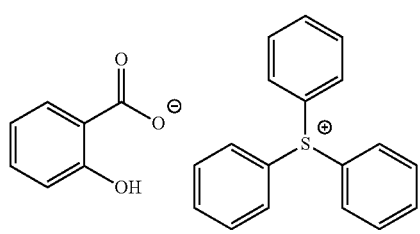
(D)-1

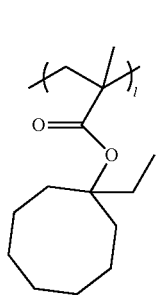

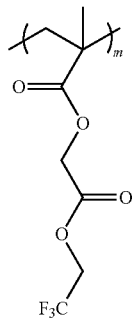

(F)-1

Molar ratio: l/m = 77/23, Mw = 23,100, Mw/Mn = 1.78

Formation of Contact Hole Pattern: Examples 1 to 4, Comparative Examples 1 to 3

An organic anti-reflection film composition (product name: ARC29A, manufactured by Brewer Science Ltd.) was applied to an 12-inch silicon wafer using a spinner, and the composition was then baked at 205° C. for 60 seconds, thereby forming an organic anti-reflection film having a film thickness of 90 nm.

Then, the resist composition was applied to the film using a spinner, and was then prebaked (PAB) on a hotplate at a bake temperature of 110° C. for 60 seconds and dried, thereby forming a resist film having a film thickness of 85 nm.

Subsequently, the resist film was selectively irradiated with an ArF excimer laser (193 nm) through a mask pattern, using an immersion lithography ArF exposure apparatus NSR-S610C (manufactured by Nikon Corporation, NA (numerical aperture)=1.30, Annular (0.98/0.78) with POLANO, immersion medium: water).

Then, a solvent development was conducted for 30 seconds using butyl acetate.

Thereafter, a post exposure bake treatment was conducted at 95° C. (PEB° C.) for 60 seconds.

As a result, the following contact hole pattern (hereafter, referred to as "CH pattern") was formed.

CH pattern: 90 nm pitch/40 nm hole, mask size 55 nm.

The obtained CH pattern was evaluated as follows.

[Evaluation of Optimum Exposure Dose (Eop)]

The optimum exposure dose Eop (mJ/cm$^2$) with which the target resist pattern was formed in the above "formation of resist pattern" was determined. The results are indicated under "Eop (mJ/cm$^2$)" in Table 2.

[Evaluation of Exposure Latitude (EL Margin)]

With respect to the exposure dose with which the above CH pattern is formed, the exposure dose with which a CH pattern having a hole of with a dimension of the target dimension ±10% was formed was determined, and the EL margin (unit: %) was determined by the following formula. The results are indicated "10% EL" in Table 2.

EL margin (%)=(|E1−E2|/Eop)×100

E1: Exposure dose (mJ/cm$^2$) with which a CH pattern having a hole diameter of 40 nm was formed E2: Exposure dose (mJ/cm$^2$) with which a CH pattern having a hole diameter of 50 nm was formed The larger the value of the "EL margin", the smaller the change in the pattern size by the variation of the exposure dose.

[Evaluation of in-Plane Uniformity (CDU) of Pattern Size]

With respect to each CH pattern obtained above, 100 holes in the CH pattern were observed from the upper side thereof using a lengthwise measuring scanning electron microscope (SEM) (product name: S-9380, manufactured by Hitachi High-Technologies Corporation; acceleration voltage: 300V), and the hole diameter (nm) of each hole was measured. From the results, the value of 3 times the standard deviation σ (i.e., 3σ) was determined. The results are indicated under "CDU (nm)" in Table 2.

The smaller the thus determined 3σ value is, the higher the level of the dimension uniformity (CD uniformity) of the plurality of holes formed in the resist film.

TABLE 2

| | Eop (mJ/cm$^2$) | 10% EL | CDU (nm) |
|---|---|---|---|
| Example 1 | 36.27 | 4.73 | 7.64 |
| Example 2 | 39.46 | 5.56 | 8.46 |
| Example 3 | 31.89 | 4.98 | 7.51 |
| Example 4 | 18.42 | 4.3 | 7.29 |
| Comparative Example 1 | 39.61 | 5.13 | 8.62 |
| Comparative Example 2 | 20.1 | 4.71 | 8.15 |
| Comparative Example 3 | 19.09 | 2.42 | 9.24 |

Production of Resist Composition 2: Examples 5 to 7, Comparative Example 4

Each component (A) and each component (B) shown in Table 1, 3.25 parts by weight of the above compound (D)-1, 4 parts by weight of the above polymeric compound (F)-1, 0.2 parts by weight of salicylic acid and 4,000 parts by weight of a solvent (a mixed solvent of PGMEA/PGME/cyclohexanone (weight ratio: 45/30/25)) were mixed together, so as to produce the resist compositions of Examples 5 to 7 and Comparative Example 4.

TABLE 3

| | Component (A) | Component (B) |
|---|---|---|
| Example 5 | (A)-3 [100] | (B)-1 [3.4] |

TABLE 3-continued

| | Component (A) | Component (B) |
|---|---|---|
| Example 6 | (A)-3 [100] | (B)-2 [4.2] |
| Example 7 | (A)-3 [100] | (B)-3 [3.2] |
| Comparative Example 4 | (A)-3 [100] | (B)-4 [3.2] |

In Table 3, the values in brackets [ ] indicate the amount (in terms of parts by weight) of the component added.

In Table 3, (A)-3 indicate polymeric compound (A)-3.

In Table 3, (B)-1 to (B)-4 indicate compounds the above compounds (B)-1 to (B)-4.

[Chemical Formula 61]

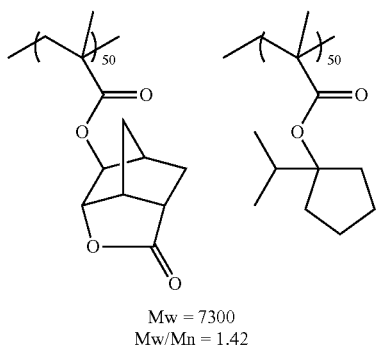

(A)-3

Mw = 7300
Mw/Mn = 1.42

Formation of Line and Space Pattern: Examples 5 to 7, Comparative Example 4

An organic anti-reflection film composition (product name: ARC29A, manufactured by Brewer Science Ltd.) was applied to an 12-inch silicon wafer using a spinner, and the composition was then baked at 205° C. for 60 seconds, thereby forming an organic anti-reflection film having a film thickness of 90 nm.

Then, each resist composition of Examples 5 to 7 and Comparative Example 4 was applied to the film using a spinner, and was then prebaked (PAB) on a hotplate at a bake temperature of 110° C. for 60 seconds and dried, thereby forming a resist film having a film thickness of 100 nm.

Subsequently, the resist film was selectively irradiated with an ArF excimer laser (193 nm) through a mask pattern, using an immersion lithography ArF exposure apparatus NSR-S610C (manufactured by Nikon Corporation, NA (numerical aperture)=1.30, Annular (0.85/0.65) with POLANO, immersion medium: water).

Then, a solvent development was conducted for 30 seconds using butyl acetate.

Thereafter, a post exposure bake treatment was conducted at 95° C. (PEB° C.) for 60 seconds.

As a result, the following line and space pattern (hereafter, referred to as "LS pattern") was formed.

LS pattern: 128 nm pitch/40 nm space, mask size 54 nm.

The obtained LS pattern was evaluated as follows.

[Evaluation of Optimum Exposure Dose (Eop)]

The optimum exposure dose Eop (mJ/cm$^2$) with which the target resist pattern was formed in the above "formation of resist pattern" was determined. The results are indicated under "Eop (mJ/cm$^2$)" in Table 4.

[Evaluation of Exposure Latitude (EL Margin)]

With respect to the exposure dose with which the above LS pattern is formed, the exposure dose with which an LS pattern having a space with a dimension of the target dimension ±10% was formed was determined, and the EL margin (unit: %) was determined by the following formula. The results are indicated "10% EL" in Table 4.

EL margin (%)=(|E1|−E2|/Eop)×100

E1: Exposure dose (mJ/cm$^2$) with which an LS pattern having a space width of 40 nm was formed E2: Exposure dose (mJ/cm$^2$) with which an LS pattern having a space width of 50 nm was formed The larger the value of the "EL margin", the smaller the change in the pattern size by the variation of the exposure dose.

[Evaluation of Minimum Width]

An LS pattern was formed by appropriately adjusting the exposure dose (mJ/cm$^2$) and the focus, and the minimum dimension of the resolved LS pattern was determined by a lengthwise measuring SEM (scanning electron microscope, acceleration voltage 300V, product name: S-9380, manufactured by Hitachi High-Technologies Corporation). The results are indicated under "Minimum space width (nm)" in Table 4.

[Evaluation of Line Width Roughness (LWR)]

With respect to the above LS pattern formed, the 3σ which is a yardstick indicating the LWR was determined.

"3σ" indicates a value of 3 times the standard deviation (σ) (i.e., 3σ (unit: nm) determined by measuring the line positions at 400 points in the lengthwise direction of the line using a scanning electron microscope (product name: S-9380, manufactured by Hitachi High-Technologies Corporation; acceleration voltage: 800V).

The smaller this 3σ value is, the lower the level of roughness on the side walls of the line, indicating that an LS pattern with a uniform width was obtained. The results are indicated under "LWR (nm)" in Table 4.

TABLE 4

| | Eop (mJ/cm$^2$) | 10% EL | Minimum space width (nm) | LWR (nm) |
|---|---|---|---|---|
| Example 5 | 20.9 | 7.05 | 49 | 6.18 |
| Example 6 | 21.8 | 8.11 | 46 | 6.71 |
| Example 7 | 19.7 | 8.65 | 44 | 5.96 |
| Comparative Example 4 | 21.7 | 6.59 | 46 | 6.95 |

As seen from the results above, the resist composition of the present invention adopting the acid generator containing the compound (B0-1) represented by general formula (b0) exhibits excellent lithography properties such as LWR and CDU.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates acid upon exposure and exhibits changed solubility in a developing solution under action of acid, the resist composition comprising:
   a component (A) which is one or more organic compounds selected from the group consisting of polymers and low molecular weight compounds and exhibits changed solubility in a developing solution under action of acid, and
   an acid-generator component (B) which generates acid upon exposure, the acid-generator component (B) comprising a compound (B0-1) represented by general formula (b0) shown below:

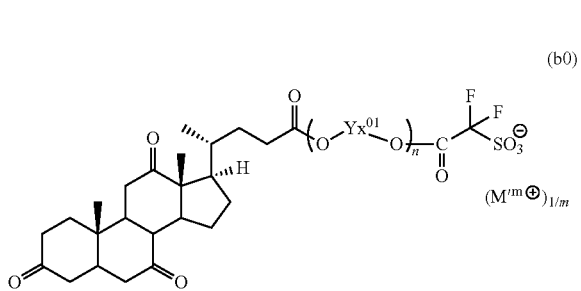

wherein $Yx^{01}$ represents a divalent linking group; n represents an integer of 1 to 3; and $M'^{m+}$ represents an organic cation having a valency of m.

2. The resist composition according to claim 1, wherein $Yx^{01}$ represents a linear or branched aliphatic hydrocarbon group of 1 to 10 carbon atoms.

3. The resist composition according to claim 2, wherein $Yx^{01}$ represents an ethylene group.

4. The resist composition according to claim 1, further comprising a photoreactive quencher component (D0).

5. A method of forming a resist pattern, comprising:
   forming a resist film on a substrate the a resist composition according to claim 1;
   exposing the resist film; and
   developing the resist film to form a resist pattern.

6. A compound represented by general formula (b0) shown below:

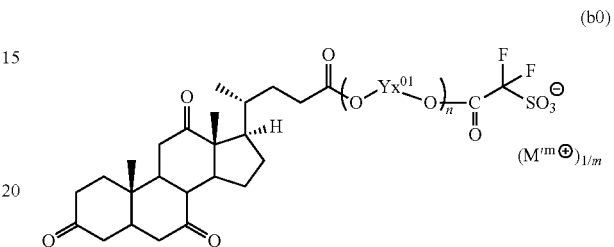

wherein $Yx^{01}$ represents a divalent linking group; n represents an integer of 1 to 3; and $M'^{m+}$ represents an organic cation having a valency of m.

7. The compound according to claim 6, wherein $Yx^{01}$ represents a linear or branched aliphatic hydrocarbon group of 1 to 10 carbon atoms.

8. The compound according to claim 6, wherein $Yx^{01}$ represents an ethylene group.

* * * * *

UNITED STATES PATENT AND TRADEMARK OFFICE
CERTIFICATE OF CORRECTION

PATENT NO. : 9,678,423 B2
APPLICATION NO. : 15/072004
DATED : June 13, 2017
INVENTOR(S) : Takashi Nagamine, Hideto Nito and Daichi Takaki Page 1 of 5

It is certified that error appears in the above-identified patent and that said Letters Patent is hereby corrected as shown below:

On the Title Page

Item (57) (abstract), Line 13, " " should be -- --.

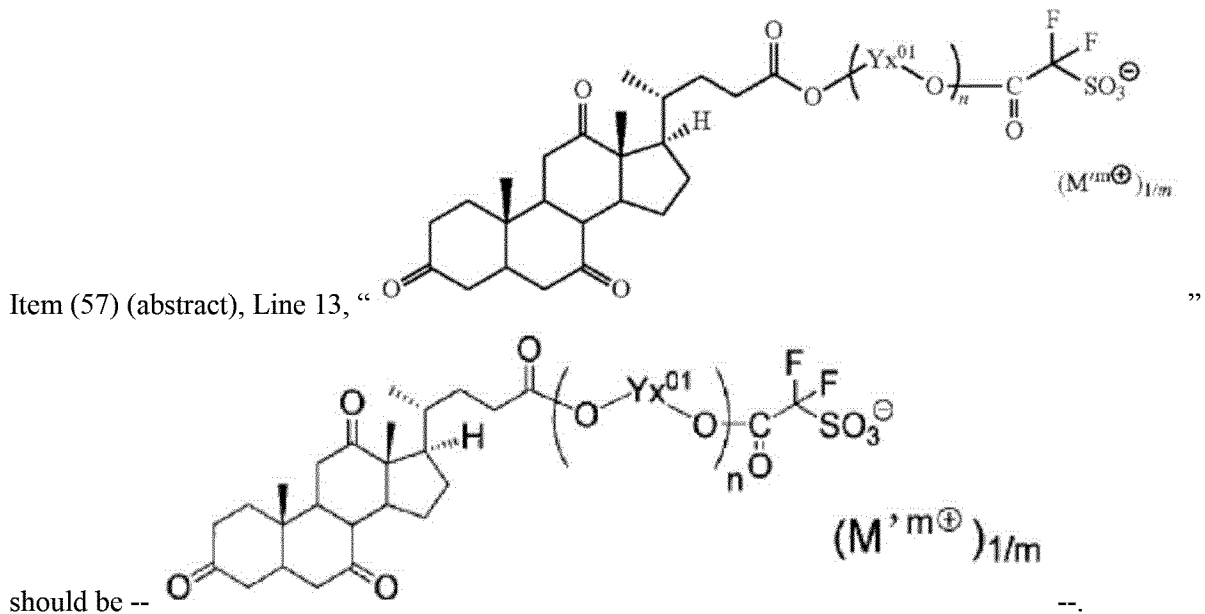

Signed and Sealed this
Second Day of October, 2018

Andrei Iancu
*Director of the United States Patent and Trademark Office*

CERTIFICATE OF CORRECTION (continued)
U.S. Pat. No. 9,678,423 B2

In the Specification

Column 2, Lines 25-33, " 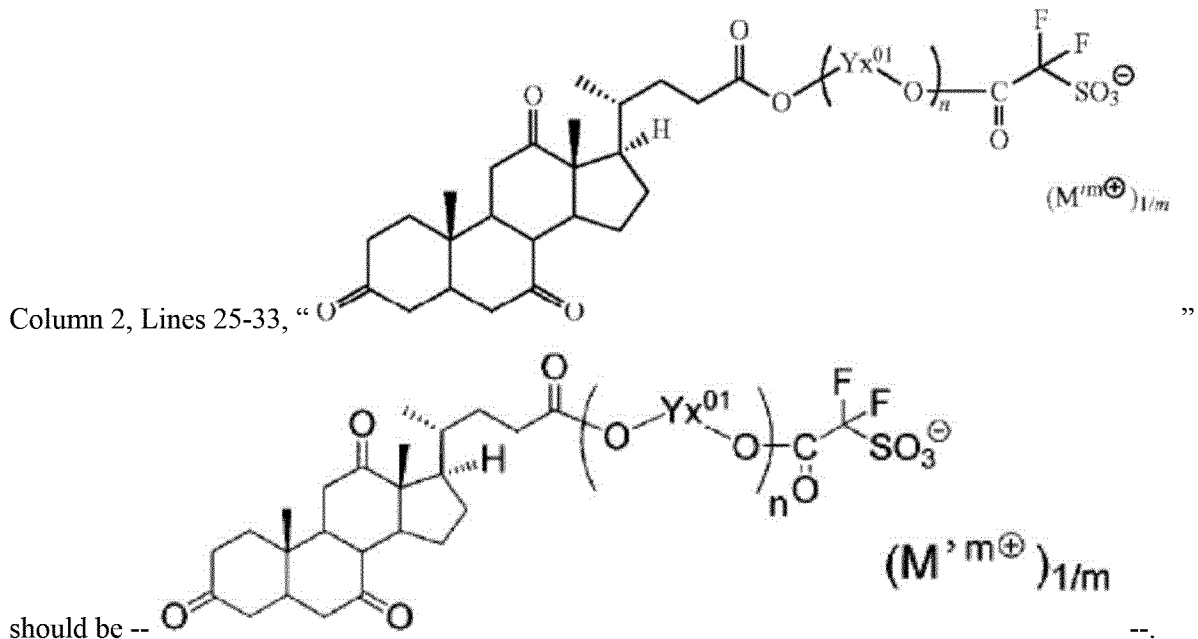 "

should be -- --.

Column 2, Lines 55-64, " 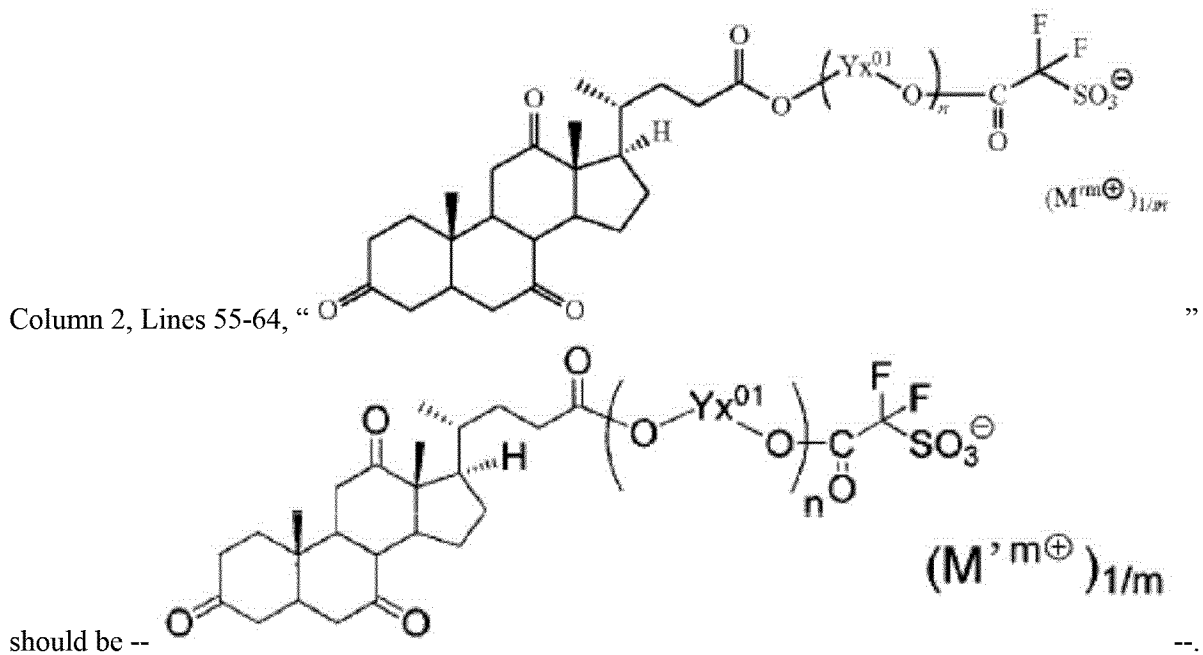 "

should be -- --.

CERTIFICATE OF CORRECTION (continued)
U.S. Pat. No. 9,678,423 B2

Column 3, Lines 7-16, " 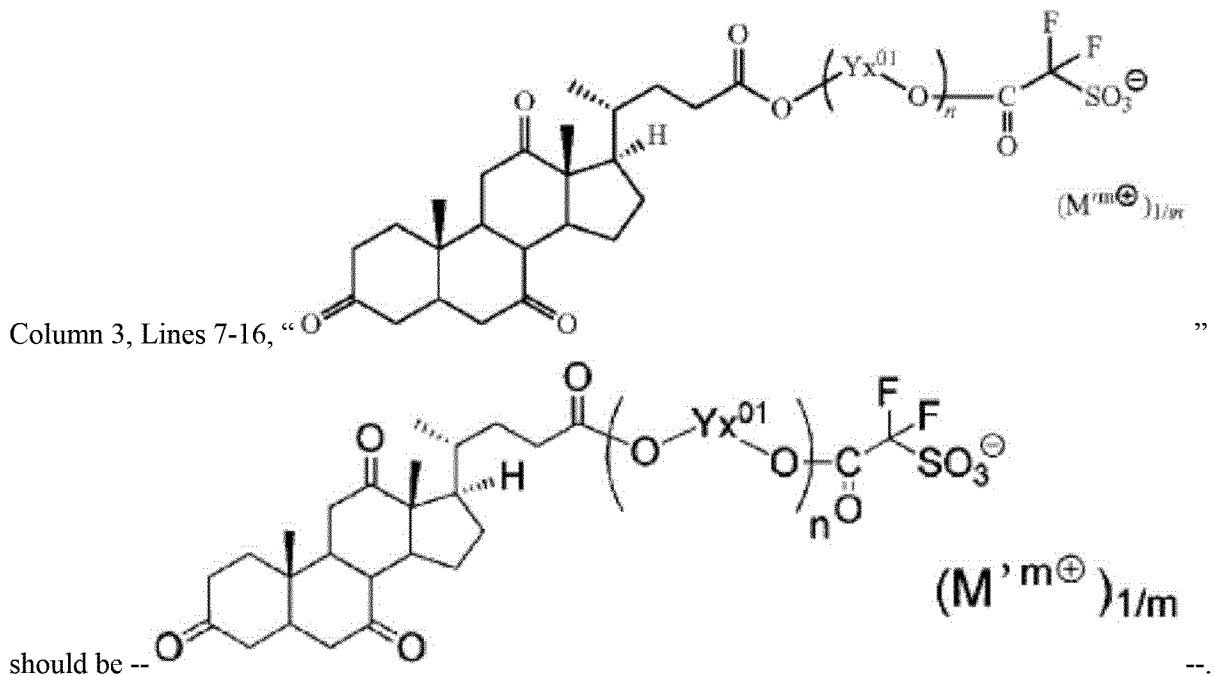 "

should be -- --.

Column 7, Lines 61-66, " 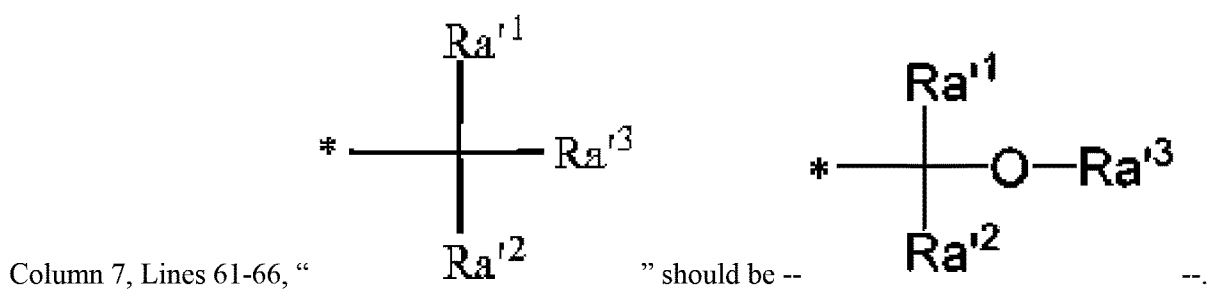 " should be -- --.

Column 53, Line 56, after "R$^{212}$" insert --may--.

Column 54, Line 1, after "R$^{212}$," insert --,--.

Column 61, Lines 21-35, " 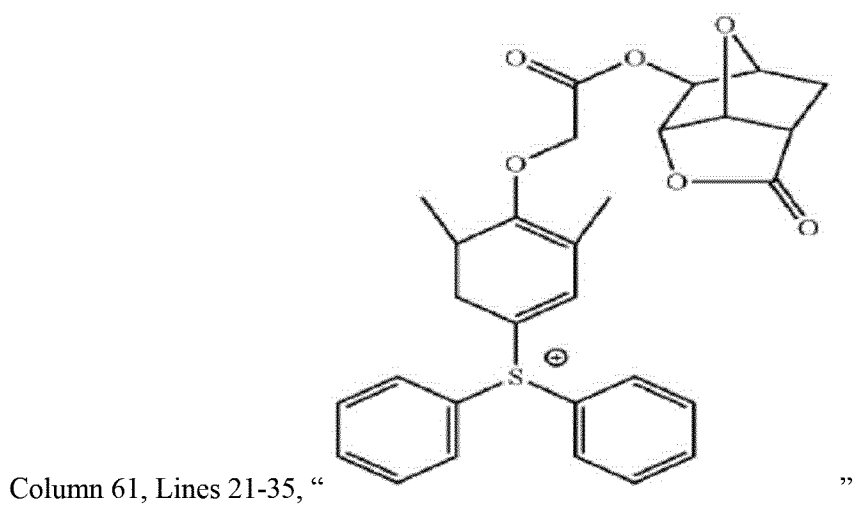 "

CERTIFICATE OF CORRECTION (continued)
U.S. Pat. No. 9,678,423 B2

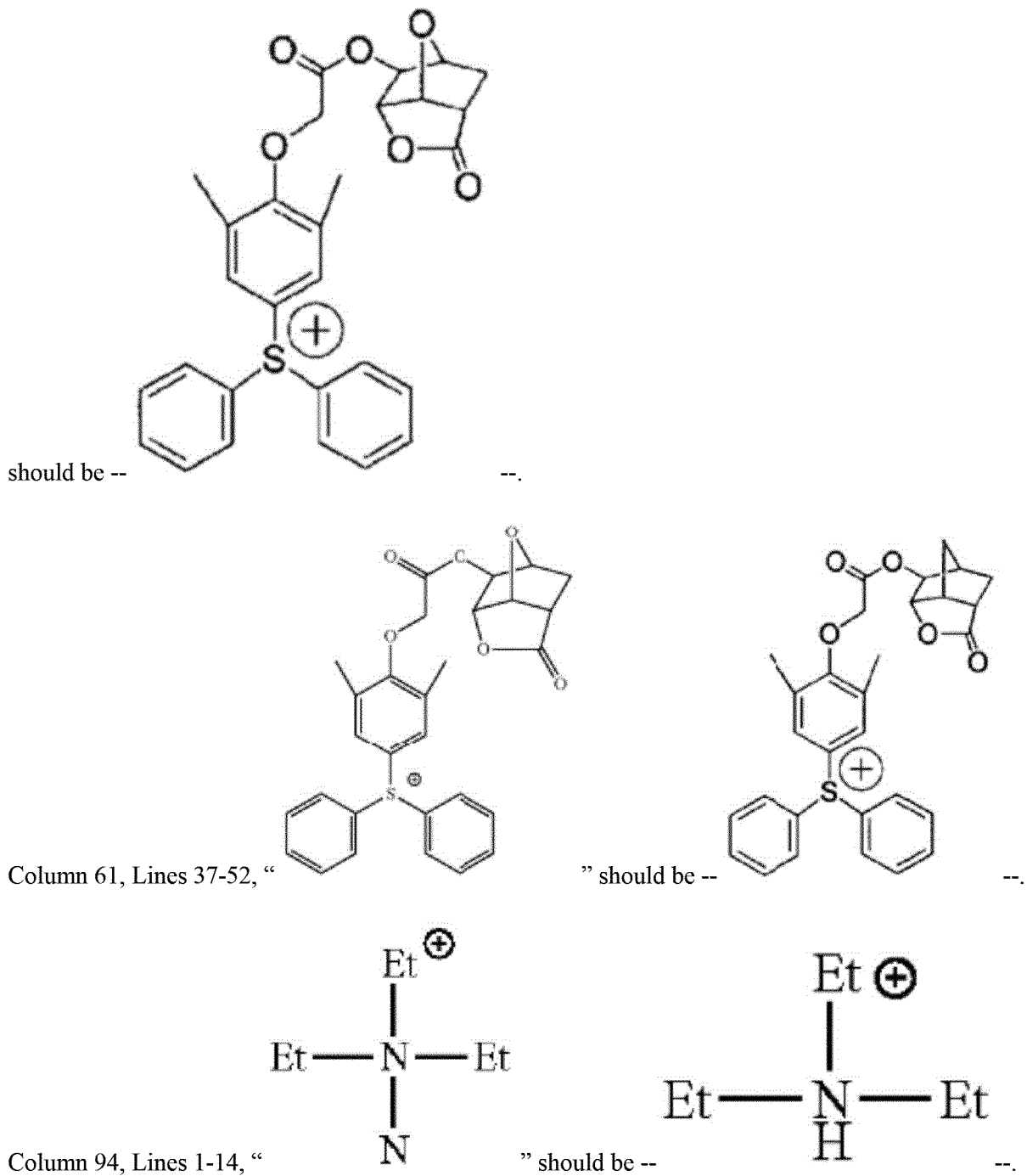

CERTIFICATE OF CORRECTION (continued)
U.S. Pat. No. 9,678,423 B2

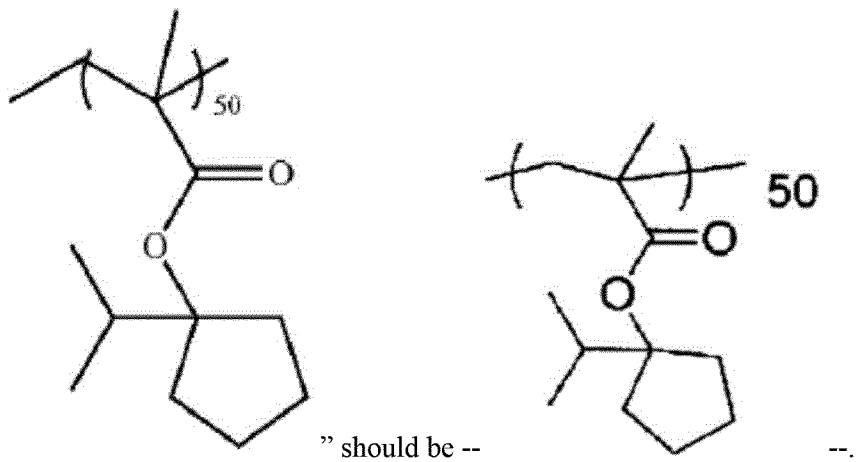

Column 105, Lines 20-29, " " should be -- --.

Column 106, Line 11, "=(lE1l-E2l/Eop)×100" should be --=(lE1-E2l/Eop)×100--.

Column 106, Line 34, "(i.e., 3σ (unit:" should be --(i.e., 3σ) (unit:--.

In the Claims

Column 108, Line 6 (Claim 5), "the a" should be --the--.